(12) United States Patent
Sides et al.

(10) Patent No.: US 10,624,794 B2
(45) Date of Patent: Apr. 21, 2020

(54) NEGATIVE PRESSURE WOUND THERAPY SYSTEMS, DEVICES, AND METHODS

(71) Applicant: Healyx Labs, Inc., Mountain View, CA (US)

(72) Inventors: Madeline Sides, San Francisco, CA (US); Robert Hutton, Los Altos, CA (US); James McCrea, San Carlos, CA (US); Lawson Fisher, Portola Valley, CA (US)

(73) Assignee: Healyx Labs, Inc., Mountain View, CA (US)

( * ) Notice: Subject to any disclaimer, the term of this patent is extended or adjusted under 35 U.S.C. 154(b) by 9 days.

(21) Appl. No.: 16/272,980

(22) Filed: Feb. 11, 2019

(65) Prior Publication Data

US 2019/0247236 A1 Aug. 15, 2019

Related U.S. Application Data

(60) Provisional application No. 62/629,185, filed on Feb. 12, 2018.

(51) Int. Cl.
*A61M 1/00* (2006.01)
*A61F 13/02* (2006.01)
(Continued)

(52) U.S. Cl.
CPC ......... *A61F 13/0216* (2013.01); *A61M 1/009* (2014.02); *A61M 1/0088* (2013.01);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| 6,010,524 A | 1/2000 | Fleischmann |
| 6,345,623 B1 | 2/2002 | Heaton et al. |

(Continued)

FOREIGN PATENT DOCUMENTS

| AU | 2014253510 B2 | 11/2016 |
| EP | 3423123 A1 | 1/2019 |

(Continued)

OTHER PUBLICATIONS

Orgill DP, Bayer LR. Negative pressure wound therapy: past, present and future. Int Wound J Dec. 2013; 10 Suppl 1:15-9.
(Continued)

*Primary Examiner* — Tatyana Zalukaeva
*Assistant Examiner* — Ilya Y Treyger
(74) *Attorney, Agent, or Firm* — Fortem IP LLP; Matthew Lincicum

(57) ABSTRACT

A negative pressure wound therapy system includes a wound dressing and a suction device configured to be in fluid communication with the wound dressing via a conduit to channel a fluid between at least the wound dressing and the suction device. The suction device includes a vacuum connection configured to be coupled to the conduit, a vacuum pump, an analog electronic pressure sensor in electrical communication with the vacuum pump, and a passive valve assembly. The passive valve assembly is in fluid communication with (1) the vacuum pump, (2), the analog electronic pressure sensor, and (3) the vacuum connection, and is configured to maintain the vacuum pump in fluid communication with the vacuum connection within a predefined pressure range, and to passively inhibit fluid communication between the vacuum pump and the vacuum connection outside of the predefined pressure range.

19 Claims, 14 Drawing Sheets

US 10,624,794 B2
Page 2

(51) Int. Cl.
　　*A61M 13/00* (2006.01)
　　*A61M 27/00* (2006.01)
　　*A61F 13/00* (2006.01)
　　*A61B 17/50* (2006.01)

(52) U.S. Cl.
　　CPC ......... *A61M 1/0031* (2013.01); *A61M 1/0092* (2014.02); *A61M 2205/15* (2013.01); *A61M 2205/3331* (2013.01); *A61M 2205/3334* (2013.01); *A61M 2205/3344* (2013.01)

(56) References Cited

U.S. PATENT DOCUMENTS

| | | |
|---|---|---|
| D469,176 S | 1/2003 | Hall et al. |
| 6,547,255 B1 | 4/2003 | Donaway et al. |
| 6,553,998 B2 | 4/2003 | Heaton et al. |
| D475,134 S | 5/2003 | Randolph |
| 6,557,704 B1 | 5/2003 | Randolph |
| 6,685,681 B2 | 2/2004 | Lockwood et al. |
| 6,695,823 B1 | 2/2004 | Lina et al. |
| 6,856,821 B2 | 2/2005 | Johnson |
| 6,994,702 B1 | 2/2006 | Johnson |
| 7,004,915 B2 | 2/2006 | Boynton et al. |
| 7,022,113 B2 | 4/2006 | Lockwood et al. |
| 7,128,735 B2 | 10/2006 | Weston |
| 7,160,273 B2 | 1/2007 | Greter et al. |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,279,612 B1 | 10/2007 | Heaton |
| 7,316,672 B1 | 1/2008 | Hunt et al. |
| D565,177 S | 3/2008 | Locke et al. |
| 7,338,482 B2 | 3/2008 | Lockwood et al. |
| 7,361,184 B2 | 4/2008 | Joshi |
| 7,438,705 B2 | 10/2008 | Karpowicz et al. |
| 7,534,240 B1 | 5/2009 | Johnson |
| 7,553,306 B1 | 6/2009 | Hunt et al. |
| 7,569,742 B2 | 8/2009 | Haggstrom et al. |
| 7,615,036 B2 | 11/2009 | Joshi et al. |
| 7,618,382 B2 | 11/2009 | Vogel et al. |
| 7,678,102 B1 | 3/2010 | Heaton |
| 7,722,582 B2 | 5/2010 | Lina et al. |
| 7,779,625 B2 | 8/2010 | Joshi et al. |
| 7,799,004 B2 | 9/2010 | Tumey |
| 7,838,717 B2 | 11/2010 | Haggstrom et al. |
| 7,909,805 B2 | 3/2011 | Weston |
| 8,007,491 B2 | 8/2011 | Pinto et al. |
| 8,021,347 B2 | 9/2011 | Vitaris et al. |
| 8,048,046 B2 | 11/2011 | Hudspeth et al. |
| 8,070,715 B2 | 12/2011 | Quackenbush et al. |
| 8,070,716 B2 | 12/2011 | Sutrina et al. |
| 8,100,887 B2 | 1/2012 | Weston et al. |
| 8,114,126 B2 | 2/2012 | Heaton et al. |
| 8,128,607 B2 | 3/2012 | Hu et al. |
| 8,177,764 B2 | 5/2012 | Hu et al. |
| 8,211,071 B2 | 7/2012 | Mormino et al. |
| 8,246,590 B2 | 8/2012 | Hu et al. |
| 8,251,979 B2 | 8/2012 | Malhi |
| 8,257,328 B2 | 9/2012 | Augustine et al. |
| 8,282,611 B2 | 10/2012 | Weston |
| 8,298,200 B2 | 10/2012 | Vess et al. |
| 8,308,714 B2 | 11/2012 | Weston et al. |
| 8,323,264 B2 * | 12/2012 | Weston ............... A61M 1/0066 604/543 |
| 8,337,474 B2 | 12/2012 | Hu et al. |
| 8,366,692 B2 | 2/2013 | Weston et al. |
| 8,403,902 B2 | 3/2013 | Locke |
| 8,435,221 B2 | 5/2013 | Hu et al. |
| 8,460,255 B2 | 6/2013 | Joshi et al. |
| 8,529,532 B2 | 9/2013 | Pinto et al. |
| 8,540,688 B2 | 9/2013 | Eckstein et al. |
| 8,545,466 B2 | 10/2013 | Andresen et al. |
| 8,556,871 B2 | 10/2013 | Fruchterman et al. |
| 8,562,576 B2 | 10/2013 | Hu et al. |
| 8,568,386 B2 | 10/2013 | Malhi |
| 8,579,872 B2 | 11/2013 | Coulthard et al. |
| 8,585,665 B2 | 11/2013 | Khosrowshahi |
| 8,591,485 B2 | 11/2013 | Lissner et al. |
| 8,628,505 B2 | 1/2014 | Weston |
| 8,641,691 B2 | 2/2014 | Fink et al. |
| 8,641,693 B2 | 2/2014 | Locke et al. |
| 8,663,198 B2 | 3/2014 | Buan et al. |
| 8,663,200 B2 | 3/2014 | Weston et al. |
| 8,715,256 B2 | 5/2014 | Greener |
| 8,734,410 B2 | 5/2014 | Hall et al. |
| 8,784,392 B2 | 7/2014 | Vess et al. |
| 8,808,259 B2 | 8/2014 | Walton et al. |
| 8,827,983 B2 | 9/2014 | Braga et al. |
| 8,829,263 B2 | 9/2014 | Haggstrom et al. |
| 8,834,434 B2 | 9/2014 | Hu et al. |
| 8,834,451 B2 | 9/2014 | Blott et al. |
| 8,852,170 B2 | 10/2014 | Weston et al. |
| 8,905,983 B2 | 12/2014 | Locke et al. |
| 8,926,575 B2 | 1/2015 | Hu et al. |
| 8,945,030 B2 | 2/2015 | Weston |
| 8,945,074 B2 | 2/2015 | Buan et al. |
| 8,956,336 B2 | 2/2015 | Haggstrom et al. |
| 8,961,481 B2 | 2/2015 | Hu et al. |
| 9,017,302 B2 | 4/2015 | Vitaris et al. |
| 9,058,634 B2 | 6/2015 | Buan et al. |
| 9,061,095 B2 | 6/2015 | Adie et al. |
| 9,067,003 B2 | 6/2015 | Buan et al. |
| 9,084,845 B2 | 7/2015 | Adie et al. |
| D738,487 S | 9/2015 | Anderson et al. |
| 9,180,231 B2 | 11/2015 | Greener |
| 9,192,700 B2 | 11/2015 | Weston et al. |
| 9,211,365 B2 | 12/2015 | Weston |
| 9,220,822 B2 | 12/2015 | Hartwell |
| 9,220,823 B2 | 12/2015 | Nicolini |
| 9,226,737 B2 | 1/2016 | Dunn |
| 9,227,000 B2 | 1/2016 | Fink et al. |
| 9,272,080 B2 | 3/2016 | Weston |
| 9,283,307 B2 | 3/2016 | Hu et al. |
| 9,289,542 B2 | 3/2016 | Blott et al. |
| 9,421,133 B2 | 8/2016 | Hu et al. |
| 9,427,505 B2 | 8/2016 | Askem et al. |
| 9,456,928 B2 | 10/2016 | Haggstrom et al. |
| 9,545,463 B2 | 1/2017 | Blott et al. |
| 9,545,465 B2 | 1/2017 | Allen et al. |
| 9,579,431 B2 | 2/2017 | Buan et al. |
| 9,585,990 B2 | 3/2017 | Karpowicz et al. |
| 9,629,986 B2 | 4/2017 | Patel et al. |
| 9,662,429 B2 | 5/2017 | Pratt et al. |
| 9,669,138 B2 | 6/2017 | Joshi et al. |
| 9,713,661 B2 | 7/2017 | Coston et al. |
| 9,901,664 B2 | 2/2018 | Askem |
| 9,974,890 B2 | 5/2018 | Hudspeth et al. |
| 9,999,711 B2 | 6/2018 | Weston et al. |
| 10,016,539 B2 | 7/2018 | Coulthard et al. |
| 10,058,642 B2 | 8/2018 | Weston |
| 10,105,472 B2 | 10/2018 | Pratt et al. |
| 10,124,093 B1 | 11/2018 | Francis et al. |
| 10,130,526 B2 | 11/2018 | Fink et al. |
| 10,143,783 B2 | 12/2018 | Adie et al. |
| 10,188,776 B2 | 1/2019 | Greener |
| 10,299,964 B2 | 5/2019 | Askem et al. |
| 10,300,178 B2 | 5/2019 | Buan et al. |
| 10,307,516 B2 | 6/2019 | Aceto et al. |
| 10,314,954 B2 | 6/2019 | Hu et al. |
| 10,322,033 B2 | 6/2019 | Hu et al. |
| 10,328,185 B2 | 6/2019 | Simmons et al. |
| 10,328,187 B2 | 6/2019 | Gordon et al. |
| 2001/0029956 A1 | 10/2001 | Argenta et al. |
| 2002/0026946 A1 | 3/2002 | McKay |
| 2002/0082567 A1 | 6/2002 | Lockwood et al. |
| 2002/0143286 A1 | 10/2002 | Tumey |
| 2002/0161317 A1 | 10/2002 | Risk et al. |
| 2002/0198503 A1 | 12/2002 | Risk et al. |
| 2003/0014022 A1 | 1/2003 | Lockwood et al. |
| 2003/0040687 A1 | 2/2003 | Boynton et al. |
| 2003/0078532 A1 | 4/2003 | Ruszczak et al. |
| 2003/0093041 A1 | 5/2003 | Risk et al. |
| 2003/0212357 A1 | 11/2003 | Pace |
| 2004/0006319 A1 | 1/2004 | Lina et al. |

(56) References Cited

U.S. PATENT DOCUMENTS

| | | |
|---|---|---|
| 2004/0064111 A1 | 4/2004 | Lockwood et al. |
| 2004/0064132 A1 | 4/2004 | Boehringer et al. |
| 2004/0073151 A1 | 4/2004 | Weston |
| 2004/0260230 A1 | 12/2004 | Randolph |
| 2005/0004534 A1 | 1/2005 | Lockwood et al. |
| 2005/0070835 A1 | 3/2005 | Joshi |
| 2005/0085795 A1 | 4/2005 | Lockwood et al. |
| 2005/0148913 A1 | 7/2005 | Weston |
| 2005/0203452 A1 | 9/2005 | Weston et al. |
| 2005/0261642 A1 | 11/2005 | Weston |
| 2006/0015087 A1 | 1/2006 | Risk et al. |
| 2006/0025727 A1 | 2/2006 | Boehringer et al. |
| 2006/0029650 A1 | 2/2006 | Coffey |
| 2007/0005028 A1 | 1/2007 | Risk et al. |
| 2007/0014837 A1 | 1/2007 | Johnson et al. |
| 2007/0016152 A1 | 1/2007 | Karpowicz et al. |
| 2007/0032762 A1 | 2/2007 | Vogel |
| 2007/0032778 A1 | 2/2007 | Heaton et al. |
| 2007/0055209 A1 | 3/2007 | Patel et al. |
| 2007/0066946 A1 | 3/2007 | Haggstrom et al. |
| 2007/0078366 A1 | 4/2007 | Haggstrom et al. |
| 2007/0118096 A1 | 5/2007 | Smith et al. |
| 2007/0179460 A1 | 8/2007 | Adahan |
| 2007/0219532 A1 | 9/2007 | Karpowicz et al. |
| 2007/0233022 A1* | 10/2007 | Henley ............... A61M 1/0088 604/305 |
| 2007/0265585 A1 | 11/2007 | Joshi et al. |
| 2008/0011667 A1 | 1/2008 | Ruschke |
| 2008/0071234 A1 | 3/2008 | Kelch et al. |
| 2008/0071235 A1 | 3/2008 | Locke et al. |
| 2008/0082059 A1 | 4/2008 | Fink et al. |
| 2008/0200906 A1 | 8/2008 | Sanders et al. |
| 2008/0234641 A1 | 9/2008 | Locke et al. |
| 2008/0281281 A1 | 11/2008 | Meyer |
| 2009/0012482 A1 | 1/2009 | Pinto et al. |
| 2009/0076467 A1 | 3/2009 | Pinto et al. |
| 2009/0163882 A1 | 6/2009 | Koch et al. |
| 2009/0234260 A1 | 9/2009 | Coward et al. |
| 2009/0254066 A1 | 10/2009 | Heaton et al. |
| 2009/0275922 A1 | 11/2009 | Coulthard |
| 2009/0299251 A1 | 12/2009 | Buan |
| 2009/0299306 A1 | 12/2009 | Buan |
| 2009/0312727 A1 | 12/2009 | Heaton |
| 2009/0312728 A1 | 12/2009 | Randolph et al. |
| 2010/0010477 A1 | 1/2010 | Augustine et al. |
| 2010/0036333 A1 | 2/2010 | Schenk, III et al. |
| 2010/0036334 A1 | 2/2010 | Heagle et al. |
| 2010/0042021 A1 | 2/2010 | Hu et al. |
| 2010/0042059 A1 | 2/2010 | Pratt |
| 2010/0042074 A1 | 2/2010 | Weston |
| 2010/0049150 A1 | 2/2010 | Braga et al. |
| 2010/0100075 A1 | 4/2010 | Weston et al. |
| 2010/0137775 A1 | 6/2010 | Hu et al. |
| 2010/0160879 A1 | 6/2010 | Weston |
| 2010/0160880 A1 | 6/2010 | Weston |
| 2010/0174251 A1 | 7/2010 | Weston |
| 2010/0185164 A1 | 7/2010 | Hartwell |
| 2010/0198173 A1 | 8/2010 | Hu et al. |
| 2010/0198174 A1 | 8/2010 | Hu et al. |
| 2010/0262094 A1 | 10/2010 | Walton et al. |
| 2010/0262126 A1 | 10/2010 | Hu |
| 2010/0268198 A1 | 10/2010 | Buan et al. |
| 2010/0286638 A1 | 11/2010 | Malhi |
| 2010/0305524 A1 | 12/2010 | Vess et al. |
| 2010/0324510 A1 | 12/2010 | Andresen et al. |
| 2011/0008179 A1 | 1/2011 | Turner |
| 2011/0015585 A1 | 1/2011 | Svedman et al. |
| 2011/0015593 A1 | 1/2011 | Svedman et al. |
| 2011/0060204 A1 | 3/2011 | Weston |
| 2011/0077604 A1 | 3/2011 | Weston |
| 2011/0077605 A1 | 3/2011 | Karpowicz et al. |
| 2011/0087177 A2 | 4/2011 | Weston |
| 2011/0087178 A2 | 4/2011 | Weston |
| 2011/0105963 A1 | 5/2011 | Hu et al. |
| 2011/0112492 A1 | 5/2011 | Scholz et al. |
| 2011/0112494 A1 | 5/2011 | Svedman et al. |
| 2011/0130691 A1 | 6/2011 | Hu et al. |
| 2011/0184362 A1 | 7/2011 | Croizat et al. |
| 2011/0224633 A1 | 9/2011 | Robinson et al. |
| 2011/0257572 A1 | 10/2011 | Locke |
| 2011/0257612 A1 | 10/2011 | Locke |
| 2012/0035562 A1 | 2/2012 | Locke |
| 2012/0053541 A1 | 3/2012 | Yao et al. |
| 2012/0109083 A1 | 5/2012 | Coulthard et al. |
| 2012/0136325 A1 | 5/2012 | Allen |
| 2012/0271256 A1 | 10/2012 | Locke et al. |
| 2012/0271257 A1* | 10/2012 | Coulthard ............ A61M 1/0031 604/319 |
| 2012/0283672 A1 | 11/2012 | Randolph |
| 2012/0302975 A1 | 11/2012 | Buan et al. |
| 2012/0302977 A1 | 11/2012 | Buan et al. |
| 2013/0289505 A1 | 10/2013 | Yao et al. |
| 2013/0296816 A1 | 11/2013 | Greener |
| 2013/0331823 A1 | 12/2013 | Askem et al. |
| 2014/0018754 A1 | 1/2014 | Mormino et al. |
| 2014/0128824 A1 | 5/2014 | Croizat et al. |
| 2014/0235957 A1* | 8/2014 | Addington .......... A61J 15/0046 600/301 |
| 2014/0276547 A1 | 9/2014 | Lonky et al. |
| 2014/0283847 A1 | 9/2014 | Sanders et al. |
| 2015/0005722 A1 | 1/2015 | Hu et al. |
| 2015/0018786 A1 | 1/2015 | Locke et al. |
| 2015/0065966 A1 | 3/2015 | Adie et al. |
| 2015/0073361 A1 | 3/2015 | Pratt et al. |
| 2015/0231314 A1 | 8/2015 | Robinson |
| 2016/0015873 A1 | 1/2016 | Robinson et al. |
| 2016/0067104 A1 | 3/2016 | Sarangapani et al. |
| 2016/0095754 A1 | 4/2016 | Andrews et al. |
| 2016/0095966 A1 | 4/2016 | Greener |
| 2016/0144082 A1* | 5/2016 | Weston ............... A61M 1/0037 604/319 |
| 2016/0184497 A1 | 6/2016 | Phillips et al. |
| 2016/0235896 A1 | 8/2016 | Mormino et al. |
| 2016/0235897 A1 | 8/2016 | Boynton et al. |
| 2016/0250398 A1 | 9/2016 | Barr et al. |
| 2017/0058143 A1 | 3/2017 | Bitler |
| 2017/0143878 A1 | 5/2017 | Tanaka |
| 2017/0182230 A1 | 6/2017 | Ingram et al. |
| 2017/0209641 A1 | 7/2017 | Mercer et al. |
| 2017/0216501 A1 | 8/2017 | Armstrong et al. |
| 2017/0224892 A1 | 8/2017 | Pratt et al. |
| 2017/0246363 A1 | 8/2017 | Pratt et al. |
| 2017/0274124 A1 | 9/2017 | Hartwell |
| 2017/0319758 A1 | 11/2017 | Eddy et al. |
| 2017/0333605 A1 | 11/2017 | Pratt et al. |
| 2017/0354767 A1 | 12/2017 | Carr et al. |
| 2018/0008756 A1 | 1/2018 | Whyte et al. |
| 2018/0104387 A1 | 4/2018 | Braga et al. |
| 2018/0104393 A1 | 4/2018 | Wu et al. |
| 2018/0140466 A1 | 5/2018 | Hunt |
| 2018/0140467 A1 | 5/2018 | Hunt |
| 2018/0140757 A1 | 5/2018 | Vess et al. |
| 2018/0140822 A1 | 5/2018 | Robinson et al. |
| 2018/0153570 A1 | 6/2018 | Ingram et al. |
| 2018/0185629 A1 | 7/2018 | Luckemeyer et al. |
| 2018/0200414 A1 | 7/2018 | Askem et al. |
| 2018/0200415 A1 | 7/2018 | Coulthard et al. |
| 2018/0214316 A1 | 8/2018 | Robinson et al. |
| 2018/0235646 A1 | 8/2018 | Locke et al. |
| 2018/0264181 A1 | 9/2018 | Gregory et al. |
| 2018/0280202 A1 | 10/2018 | Pratt et al. |
| 2018/0304065 A1 | 10/2018 | Armstrong et al. |
| 2018/0326129 A1 | 11/2018 | Askem et al. |
| 2019/0001030 A1 | 1/2019 | Braga et al. |
| 2019/0001032 A1 | 1/2019 | Weston et al. |
| 2019/0009010 A1 | 1/2019 | Locke et al. |
| 2019/0022289 A1 | 1/2019 | Pratt et al. |
| 2019/0053819 A1 | 2/2019 | Locke et al. |
| 2019/0125943 A1 | 5/2019 | Askem et al. |
| 2019/0142644 A1 | 5/2019 | Askem et al. |
| 2019/0143007 A1 | 5/2019 | Askem et al. |
| 2019/0151156 A1 | 5/2019 | Kieswetter et al. |
| 2019/0167863 A1 | 6/2019 | Adie et al. |
| 2019/0167866 A9 | 6/2019 | Hu et al. |

(56) References Cited

U.S. PATENT DOCUMENTS

| | | |
|---|---|---|
| 2019/0192746 A1 | 6/2019 | Buan et al. |
| 2019/0231600 A1 | 8/2019 | Locke et al. |
| 2019/0231939 A1 | 8/2019 | Askem et al. |
| 2019/0231946 A1 | 8/2019 | Gregory et al. |

FOREIGN PATENT DOCUMENTS

| | | |
|---|---|---|
| EP | 3454917 A1 | 3/2019 |
| EP | 3463501 A1 | 4/2019 |
| EP | 3493860 A1 | 6/2019 |
| EP | 3311856 B1 | 7/2019 |
| IN | 201717018948 A | 11/2017 |
| IN | 201717018954 A | 11/2017 |
| IN | 201717018956 A | 11/2017 |
| IN | 201717018960 A | 11/2017 |
| WO | WO 2009047524 A2 | 4/2009 |
| WO | WO 2009016603 A3 | 7/2009 |
| WO | WO 2011124388 A1 | 10/2011 |
| WO | WO 2012027913 A1 | 3/2012 |
| WO | WO 2013064852 A1 | 5/2013 |
| WO | WO 2017077226 A1 | 5/2017 |
| WO | WO 2017077227 A1 | 5/2017 |
| WO | WO 2017197357 A1 | 11/2017 |
| WO | WO 2018130466 A1 | 7/2018 |
| WO | WO 2018136232 A1 | 7/2018 |
| WO | WO 2018158250 A1 | 9/2018 |
| WO | WO 2018162613 A1 | 9/2018 |
| WO | WO 2018164803 A1 | 9/2018 |
| WO | WO 2018167199 A1 | 9/2018 |
| WO | WO 2018170151 A1 | 9/2018 |
| WO | WO 2018186941 A1 | 10/2018 |
| WO | WO 2018150267 A3 | 11/2018 |
| WO | WO 2018158250 A4 | 11/2018 |
| WO | WO 2018206420 A1 | 11/2018 |
| WO | WO 2019083966 A1 | 5/2019 |
| WO | WO 2019086341 A1 | 5/2019 |
| WO | WO 2019086475 A1 | 5/2019 |
| WO | WO 2019113091 A1 | 6/2019 |
| WO | WO 2019129581 A2 | 7/2019 |
| WO | WO 2019135900 A1 | 7/2019 |
| WO | WO 2019139829 A1 | 7/2019 |
| WO | WO 2019140448 A1 | 7/2019 |
| WO | WO 2019152140 A1 | 8/2019 |

OTHER PUBLICATIONS

R. Nussbaum, Samuel & Carter, Marissa & E. Fife, Caroline & DaVanzo, Joan & Haught, Randall & Nusgart, Marcia & Cartwright, Donna. (2017). An Economic Evaluation of the Impact, Cost, and Medicare Policy Implications of Chronic Nonhealing Wounds. Value in Health. 21. 10.1016/j.jval.2017.07.007.
Kanakaris NK, Thanasas C, Keramaris N, Kontakis G, Granick MS, Giannoudis PV. The efficacy of negative pressure wound therapy in the management of lower extremity trauma: Review of clinical evidence. Injury 2007; 38(5): S8-S17.
Krug E, Berg L, Lee C, Hudson D, Birke-Sorensen H, Depoorter M et al. Evidence-based recommendations for the use of Negative Pressure Wound Therapy in traumatic wounds and reconstructive surgery: Steps towards an international consensus. Injury2011; 42: S1-S12.
Llanos S, Danilla S, Barraza C, Armijo E, Pieros JL, Quintas M et al. Effectiveness of Negative Pressure Closure in the Integration of Split Thickness Skin Grafts. Annals of Surgery 2006; 244(5):700-705.
Blume PA, Key JJ, Thakor P, Thakor S, Sumpio B. Retrospective evaluation of clinical outcomes in subjects with split-thickness skin graft: comparing V.A.C.® therapy and conventional therapy in foot and ankle reconstructive surgeries. International Wound Journal 2010; 7(6): 480-487.
Stannard JP, Volgas DA, Stewart R, McGwin G, Alonso JE. Negative Pressure Wound Therapy After Severe Open Fractures: A Prospective Randomized Study. Journal of Orthopaedic Trauma 2009; 23(8): 552-557.
Schlatterer DR, Hirschfeld AG, Webb LX. Negative pressure wound therapy in grade IIIB tibial fractures: fewer infections and fewer flap procedures? Clin Orthop Relat Res 2015; 473(5): 1802-1811.
Sjogren J, Gustafsson R, Nilsson J, Malmsjo M, Ingemansson R. Clinical outcome after poststernotomy mediastinitis: vacuum-assisted closure versus conventional treatment. Ann Thorac Surg 2005; 79(6): 2049-2055.
Ubbink DT, Westerbos SJ, Nelson EA, Vermeulen H. A systematic review of topical negative pressure therapy for acute and chronic wounds British Journal of Surgery 2008; 95(6): 685-692.
Szmyt K, Lukasz K, Bobkiewicz A, Cybulka B, Ledwosinski W, Gordon M et al. Comparison of the effectiveness of the treatment using standard methods and negative pressure wound therapy (NPWT) in patients treated with open abdomen technique. Pol Przegl Chir 2015; 87(1): 22-30.
Sermoneta D, Di Mugno M, Spada PL, Lodoli C, Carvelli ME, Magalini SC et al. Intra-abdominal vacuum-assisted closure (VAC) after necrosectomy for acute necrotising pancreatitis: preliminary experience. International Wound Journal 2010; 7(6): 525-530.
Mouës CM, Vos MC, Van Den Bemd G-JCM, Stijnen T, Hovius SER. Bacterial load in relation to vacuum-assisted closure wound therapy: A prospective randomized trial. Wound Repair and Regeneration 2004;12(1): 11-17.
Mandal A. Role of topical negative pressure in pressure ulcer management. Journal of Wound Care 2007; 16(1): 33-35.
Armstrong DG, Lavery LA. Negative pressure wound therapy after partial diabetic foot amputation: a multicentre, randomised controlled trial. The Lancet 2005; 366(9498): 1704-1710.
Blume PA, Walters J, Payne W, Ayala J, Lantis J. Comparison of Negative Pressure Wound Therapy Using Vacuum-Assisted Closure With Advanced Moist Wound Therapy in the Treatment of Diabetic Foot Ulcers: A multicenter randomized controlled trial. Diabetes Care 2007; 31(4): 631-636.
Nadler A, Hong NY, Lin WK, Sakharam JA. Effectiveness of bridge V.A.C. dressings in the treatment of diabetic foot ulcers. Diabetic Foot & Ankle 2011; 2(0).
Ulusal AE. Negative pressure wound therapy in patients with diabetic foot. Acta Orthopaedica et Traumatologica Turcica 2011; 45: 254-260.
Eneroth M, van Houtum WH. The value of debridement and Vacuum-Assisted Closure (V.A.C.) Therapy in diabetic foot ulcers. Diabetes/Metabolism Research and Reviews 2008; 24(S1): S76-S80.
Vuerstaek JD, Vainas T, Wuite J, Nelemans P, Neumann MH, Veraart JC. State-of-the-art treatment of chronic leg ulcers: A randomized controlled trial comparing vacuum-assisted closure (V.A.C.) with modern wound dressings. J Vasc Surg 2006; 44(5): 1029-1037; discussion 1038.
Rezzadeh KS, Nojan M, Buck A, Li A, Vardanian A, Crisera C et al. The use of negative pressure wound therapy in severe open lower extremity fractures: identifying the association between length of therapy and surgical outcomes. J Surg Res 2015.
Morykwas MJ, Argenta LC, Shelton-Brown EI, McGuirt W. Vacuum-assisted closure: a new method for wound control and treatment: animal studies and basic foundation Ann Plast Surg 1997; 38:553-62.
Borgquist, Ola, et al. "The Influence of Low and High Pressure Levels during Negative-Pressure Wound Therapy on Wound Contraction and Fluid Evacuation." Plastic and Reconstructive Surgery, vol. 127, No. 2, 2011, pp. 551-559., doi:10.1097/prs.0b013e3181fed52a.
Hyldig, N., Birke-Sorensen, H., Kruse, M., Vinter, C., Joergensen, J. S., Sorensen, J. A., Mogensen, O., Lamont, R. F., . . . Bille, C. (2016). Meta-analysis of negative-pressure wound therapy for closed surgical incisions. The British journal of surgery, 103(5), 477-86.
Dragu, Adrian, et al. "Wide Topical Negative Pressure Wound Dressing Treatment for Patients Undergoing Abdominal Dermolipectomy Following Massive Weight Loss." Obesity Surgery, vol. 21, No. 11, 2010, pp. 1781-1786., doi:10.1007/s11695-010-0328-3.
Heller, Lior, et al. "Management of Abdominal Wound Dehiscence Using Vacuum Assisted Closure in Patients with Compromised

(56) References Cited

OTHER PUBLICATIONS

Healing." The American Journal of Surgery, vol. 191, No. 2, 2006, pp. 165-172., doi:10.1016/j.amjsurg.2005.09.003.
Rao, M., et al. "The Use of Vacuum-Assisted Closure of Abdominal Wounds: a Word of Caution." Colorectal Disease, vol. 9, No. 3, 2007, pp. 266-268., doi:10.1111/j.1463-1318.2006.01154.x.
Labler, Ludwig, et al. "V.A.C.® Abdominal Dressing System." European Journal of Trauma, vol. 31, No. 5, 2005, pp. 488-494., doi:10.1007/s00068-005-2031-y.
Herscovici, Dolfi, et al. "Vacuum-Assisted Wound Closure (VAC Therapy) for the Management of Patients With High-Energy Soft Tissue Injuries." Journal of Orthopaedic Trauma, vol. 17, No. 10, 2003, pp. 683-688., doi:10.1097/00005131-200311000-00004.
Leininger, Brian E., et al. "Experience With Wound VAC and Delayed Primary Closure of Contaminated Soft Tissue Injuries in Iraq." The Journal of Trauma: Injury, Infection, and Critical Care, vol. 61, No. 5, 2006, pp. 1207-1211., doi:10.1097/01.ta.0000241150.15342.da.
Defranzo, A. J., et al. "The Use of Vacuum-Assisted Closure Therapy for the Treatment of Lower-Extremity Wounds with Exposed Bone." Plastic and Reconstructive Surgery, vol. 108, No. 5, 2001, pp. 1184-1191., doi:10.1097/00006534-200110000-00013.
Scherer, Lynette A., et al. "The Vacuum Assisted Closure Device." Archives of Surgery, vol. 137, No. 8, 2002, doi:10.1001/archsurg.137.8.930.
Kamolz, L.-P, et al. "Use of Subatmospheric Pressure Therapy to Prevent Burn Wound Progression in Human. First Experiences." Burns, vol. 30, No. 3, 2004, pp. 253-258., doi:10.1016/j.burns.2003.12.003.
Eginton, Mark T., et al. "A Prospective Randomized Evaluation of Negative-Pressure Wound Dressings for Diabetic Foot Wounds." Annals of Vascular Surgery, vol. 17, No. 6, 2003, pp. 645-649., doi:10.1007/s10016-003-0065-3.
Dorafshar A.H., Franczyk M., Gottlieb L.J., Wroblewski K.E., Lohman R.F. A prospective randomized trial comparing subatmospheric wound therapy with a sealed gauze dressing and the standard vacuum-assisted closure device. *Ann Plast Surg.* 2011;69:79-84.
Othman, D. Negative pressure wound therapy literature review of efficacy, cost effectiveness, and impact on patients' quality of life in chronic wound management and its implementation in the United Kingdom. *Plast Surg Int.* 2012;2012:374398.

Mouës CM, van den Bemd GJ, Meerding WJ, et al. An economic evaluation of the use of TNP on full-thickness wounds. *J Wound Care.* 2005;14:224-227.
Apelqvist J, Armstrong DG, Lavery LA, et al. Resource utilization and economic costs of care based on a randomized trial of vacuum-assisted closure therapy in the treatment of diabetic foot wounds. *Am J Surg.* 2008;195:782-788.
Molnar JA, Simpson JL, Voignier DM, et al. Management of an acute thermal injury with subatmospheric pressure. *J Burns Wounds.* 2005;4:e5.
Apelqvist J, Armstrong D, Augustin M, et al. (2008). Vacuum assisted closure: Recommendations for use—A consensus document. *International Wound Journal.* 5. iii-19. 10.1111/j.1742-481X.2008.00537.x.
Chio EG, Agrawal A. A randomized, prospective, controlled study of forearm donor site healing when using a vacuum dressing. *Otolaryngol Head Neck Surg.* 2010;142:174-178.
MacDonald, John M., and Mary Jo. Geyer. *Wound and Lymphoedema Management.* WHO, 2010, *Wound and Lymphoedema Management.*
Khanbhai, Mustafa & Burke, Joshua & Morley, Rachael. (2014). Using portable negative pressure wound therapy devices in the home care setting. Smart Homecare Technology and TeleHealth. 2014. 129. 10.2147/SHTT.S53413.
Geir Stray Andreassen & Jan Erik Madsen (2006) A simple and cheap method for vacuum-assisted wound closure, Acta Orthopaedica, 77:5, 820-824, DOI: 10.1080/17453670610013051.
Brown J. Machen H, Kawaza K, Mwanza Z, Iniguez S, Lang H, et al. (2013) A High-Value, Low-Cost Bubble Continuous Positive Airway Pressure System for Low-Resource Settings: Technical Assessment and Initial Case Reports. PLoS ONE 8(1): e53622. https://doi.org/10.1371/journal.pone.0053622.
Mohsin, Mir, et al. "Role of Customised Negative-Pressure Wound Therapy in the Integration of Split-Thickness Skin Grafts: A Randomised Control Study." *Indian Journal of Plastic Surgery*, vol. 50, No. 01, 2017, pp. 043-049., doi:10.4103/ijps.ijps_196_16.
Ranjeet, N, and Au Dy. "Modified Negative Pressure Wound Therapy (Modified NPWT): An Experience of 128 Cases." *Nepal Journal of Medical Sciences*, vol. 1, No. 2, 2012, pp. 108-114., doi:10.3126/njms.v1i2.6610.
Zurovcik, Danielle R., et al. "Simplified Negative Pressure Wound Therapy Device for Application in Low-Resource Settings." Journal of Orthopaedic Trauma, vol. 29, 2015, doi:10.1097/bot.0000000000000410.

* cited by examiner

| Condition Reference Number | Vacuum Level Reference Location | Vacuum Level Force Comparison | System State | Function of element in certain embodiments |
|---|---|---|---|---|
| 1 | Internal Chamber 411 | Greater than force of spring 423 in plunger assembly 415 | Plunger 425 moves away from sealing surface within cap 405, connecting points 433 and 435 to Chamber 411 | Check valve or one-way valve function that maintains negative pressure in system. |
| 2 | Internal Chamber 411 | Greater than force of spring 417 in plunger assembly 413 | Plunger 419 moves away from sealing surface within cap 403, connecting points 429 and 431 to Chamber 411 | Over Vacuum valve that relieves system vacuum pressure if it exceeds a certain maximum level. |
| 3 | Internal Chamber 411 | Less than or equal to force of spring 423 in plunger assembly 415 | Spring 415 holds plunger 425 against sealing surface within cap 405, separating Chamber 411 from points 433 and 435. | One-way valve function that prevents any positive pressure from entering points 433 and 435. Prevents backflow to wound. |
| 4 | Internal Chamber 411 | Less than or equal to force of spring 417 in plunger assembly 413 | Spring 413 holds plunger 419 against sealing surface within cap 403, separating Chamber 411 from points 429 and 431. | Seals the system from ambient vents 429 and 431 such that negative pressure is maintained. |

*Figure 4E*

NEGATIVE PRESSURE WOUND THERAPY SYSTEMS, DEVICES, AND METHODS

CROSS-REFERENCE TO RELATED APPLICATIONS

This application claims the benefit of priority to U.S. Provisional Application No. 62/629,185, filed Feb. 12, 2018, which is hereby incorporated by reference in its entirety.

TECHNICAL FIELD

The present technology relates to devices and methods for using negative pressure to treat wounds. In particular, the present technology is negative pressure wound therapy (NPWT) devices that are portable, reusable, easy to use, and economical.

BACKGROUND

Severe wounds are an urgent, unaddressed health need in resource-constrained settings. The incidence of these wounds exceeds 110 million worldwide and is growing due to an increase in diseases associated with chronic wounds—diabetes, cardiovascular disease, and obesity—and an aging global population. In the U.S., conservative estimates exceed $28 billion spent each year treating chronic wounds as a primary diagnosis. In developing world settings, etiological factors that lead to severe wounds are compounded by parasitic, bacterial, viral exposure, and road accidents. In both developed and developing world settings, these open wounds are an enormous cause of morbidity and impose a significant financial burden on patients and their families, especially as non-healing wounds may lead to prolonged disability and prevent a return to employment. The negative socio-economic impact of a chronic wound places a strain on the individual, family, and healthcare system. Without access to adequate wound care treatment in resource-constrained settings, patients suffer from long and costly healing processes. Quality of life is worsened by pain, emotional stress, impaired physical mobility, and often isolation. Direct healthcare costs and opportunity costs in an absence from work and/or loss of employment can devastate a patient's entire family. Hospital systems, outpatient facilities, and home-care settings are burdened with overcrowding and excessive resource requirements.

Therapeutic challenges in wound healing amplify this devastating crisis. Highly orchestrated and specialized procedures are required to treat these chronic wounds. This dynamic process involves the removal of debris, control of infection, reduction of inflammation to clear the area for angiogenesis, deposition of granulation tissue, wound contraction and maturation—a sequence leading to repair and closure. A failure in just one step of this complex process may inhibit healing progression. Neglect present in wound care can lead to further morbidity and increase mortality rates. The cascade effect from infection to systemic complications, extensive hospitalization, amputation and death is inevitable if there is no effective intervention.

The current standard in wound care in many resource-constrained settings is limited to daily gauze dressing wraps and debridement. As gauze dressings are non-occlusive, or permeable to exogenous bacteria, treatment with gauze wraps introduces greater risk of infection, requiring frequent dressing changes and resulting in a prolonged wound healing period. These dressings are also associated with high medical costs, time-consuming care, and patient discomfort.

Negative Pressure Wound Therapy (NPWT) is a clinically validated and market proven method of treating severe wounds. This clinically validated advanced wound management technology addresses the needs of acute, chronic, and postoperative wound care. Typically, the therapy includes a vacuum suction device that applies negative pressure across the surface of a wound through a sealed dressing covering the wound site. The dressing is typically a porous foam or gauze-based material that is fitted to the contours of the wound and covered with an adhesive, airtight film A canister typically connects the dressing and vacuum suction device. A canister is a fluid container that collects and stores fluids pulled out of the wound with negative pressure. The application of continuous negative pressure (suction) over a wound area leads to the removal of exudate (excess fluid), improved vascularization, and creates mechanical forces that stimulate a biological response, leading to significantly faster wound healing. Moreover, NPWT creates a moist microenvironment for the wound, conducive to cell proliferation and migration, angiogenesis, and the elimination of necrotic tissue.

NPWT has been validated as a treatment for a variety of wounds, including pressure ulcers, diabetic foot ulcers, burns and post-traumatic wounds. The role of NPWT in continuous treatment includes a multitude of specific healing-related benefits, such as reduction in wound size and volume as well as decreased healing time for open wounds by a factor of two or more. Blood flow has shown up to a fivefold increase during treatment and edema reduction is significant. Patients treated with a NPWT device, commonly referred to as a "wound vacuum" display higher rates of granulation tissue and up to a threefold increase in expression of enzymes and growth factors at the wound bed. In practice, NPWT is proven to reduce wound-related complications, including infection rate and re-amputations, and increase patient survival when compared to standard treatment. The healing of chronic and acute wounds can be a multi-week or multi-month process, even when NPWT is used. For example, Medicare in the US covers up to four months of treatment with NPWT devices. While NPWT has been shown to be a useful tool in wound care, currently-marketed NPWT products are not aligned with the needs of users in resource-constrained healthcare settings, remote/home use settings and/or low-income population segments. Consequently, currently marketed NPWT devices, including reusable stand-alone devices and portable/disposable devices, may be out of reach financially or difficult to use successfully in these settings. Wound incidence is equivalent if not greater in these patient segments and settings, which underscores a need for technology that can be accessed by these patients and their caregivers.

Reusable, stand-alone NPWT devices are larger systems designed for inpatient settings that can be used many times for repeated treatment and enable healthcare providers to customize the therapy by adjusting a variety of settings. The primary application of this product segment has been the treatment of large non-healing wounds with high volumes of exudate. These reusable stand-alone devices are limited by elaborate user interfaces, complex internal structures (making them susceptible to failures and software bugs), burdensome power requirements and large size. These limitations additionally contribute to a high per device production cost. User interface (UI) complexity in stand-alone devices is evidenced by added features like touch screens and LCD screens, which, while offering a highly customizable treatment regimen, also require users to be trained in device operation and have a moderate level of technological literacy for successful device use and monitoring. UI complexity is further evident in the physical mechanisms used to connect and disconnect device accessories, such as canisters and wound dressings. These mechanisms require adequate physical dexterity from users to twist, orient or locate specific parts in order to make an airtight seal in the system, an essential condition for wound therapy. This can be an obstacle for many wound patients, who often have limited dexterity due to age or co-morbidities. Further, these complex mechanisms are subject to breakage through normal wear and tear or user error, and may be hard to service onsite due to the specific tools, skills and parts required for their repair. The internal apparatuses that constitute current standalone devices feature intricate mechanical and electronic mechanisms. These devices may use a number of electromechanical valves, sensors of various types and microprocessors or microcontrollers for system control in combination with one or more electric vacuum pumps. These components enable high-precision control and monitoring of system pressure and flow rates, but also make the system susceptible to electrical or software bugs, or breakdown of processors or sensors that interrupt the delivery of therapy. Due to these abovementioned factors, often NPWT device manufacturers and suppliers must train personnel extensively to operate and troubleshoot each NPWT device to avoid user errors and/or patient risk. This requirement limits device use to settings with qualified and available trained personnel. Further, standalone devices can only be used in locations with a stable AC power source because components used to create these complex UIs and pressure/flow rate controls draw more power than can be continuously supplied by a single battery or battery pack. These components also make devices large and heavy. Finally, many of these abovementioned limitations have financial consequences for consumers and healthcare providers in that they increase the cost of device production and implementation.

Disposable NPWT devices (single-use) are typically battery-powered highly portable treatment systems that may or may not be re-chargeable. Their UIs are more streamlined, often with a power indicator, power button and no ability to change canisters (e.g. a single-use canister fully enclosed in a device). These devices are typically smaller in size and weight than stand-alone devices. This emerging sector of NPWT devices offers substantial benefits in simplifying treatment, but it is limited to small, fast-healing wounds as the devices typically last only 7 days and can only be used to contain a relatively small amount of exudate (70-300 mL) before needing to be replaced. While these devices have a simplified control UI, they may still have complex attachment mechanisms for accessories that are susceptible to failure, much like stand-alone devices. Additionally, they may have similar internal complexity to stand-alone devices in terms of components used to achieve pressure control, which drives up production cost while making the devices susceptible to software bugs and component failures (e.g. microprocessors, microcontrollers, etc.). Commercially available portable systems address some of the size, complexity and power requirement limitations of standalone devices, to encourage ambulatory patients to move around while receiving treatment. These devices are lower cost and less complex. However, these devices were tailored to exclusively address specific wound types such as acute incision wounds or surgical site infections. This narrower focus limits the indications for use, especially large wounds with high volumes of exudate. Additionally, a shorter useful lifespan makes the devices less economical and practical in chronic wound care.

Within the Disposable NPWT device (single-use) segment, a subgroup of non-electrically powered devices (manual) have been introduced in the marketplace. These non-electric devices provide similar benefits to the aforementioned powered, single-use devices—streamlined UI, portability, reduced production cost. They are also similarly limited in application due to narrower indications for use (e.g. smaller wounds with lower volumes of exudate) and shorter useful lifespan. The manually powered suction apparatus provides an added benefit by reducing reliance on wall and/or battery power and the internal mechanisms for vacuum generation and pressure control do not rely on expensive electrical components (e.g. microprocessors, microcontrollers, etc.). However, the usefulness of manual systems is limited because they are not able to accurately control system pressure, which is a critical NPWT parameter in clinical practice. Though less susceptible to software bugs or electrical component failures, manual devices generate vacuum pressure without any feedback and ability to self-correct if vacuum pressure drops. The manual system requires significant user attention to maintain a vacuum seal and to reestablish clinically appropriate vacuum pressure if pressure is lost for any reason.

Accordingly, there is a need for improved NPWT systems that are robust, reusable, portable, economical, clinically effective, power-efficient and have streamlined interfaces for ease-of-use even among unskilled populations. Finally, both standalone and portable units currently on the market are limited by designs that require a particular brand or type of accessories (waste canister and wound dressing). These units become completely unusable if a single piece of a particular accessory is unavailable or out of supply. This constraint interrupts therapy, drives up prices and makes NPWT infeasible in regions where medical supply chains are frequently interrupted. For these reasons, there remains a need to develop improved solutions that reduce cost, reduce complexity, and increase robustness and accessibility of the therapy to patients.

SUMMARY

The present technology is directed to devices, systems, and methods for negative pressure wound therapy (NPWT). The present technology is illustrated, for example, according to various aspects described herein with reference to FIGS. 1A-8.

Embodiments of the present technology are directed to NPWT systems that are simplified for ease-of-use, streamlined for cost-effectiveness, and designed for portability, robustness and reusability, through a combination of mechanical, electronic and electromechanical features. For example, simplified NPWT systems in accordance with the present technology can be configured to provide only a single level of negative pressure that is not adjustable by the user, so as to provide the appropriate and physician-prescribed level of suction (i.e. the therapeutic vacuum level) for effective NPWT without requiring user input or expertise. The system can also be configured such that the only user input to deliver therapy at a particular vacuum level setting, apart from placing the dressing over the wound, is pressing a power button to initiate or to terminate treatment. In some embodiments, the device user interface can omit any digital output display to reduce cost and complexity. In some embodiments, the device can contain various types of waste canisters with volumes sufficient to treat wounds with low to high rates of exudate production for several days. In some embodiments, this canister is fluidically coupled to the device with an easy-to-use external connector piece. The benefits of the present technology include robustness in care settings without trained users to initiate and support therapy and/or a reliable source of wall power, as well as reduced device cost and reduced device weight, all of which increase device accessibility for resource-constrained care settings and patients.

Various examples of aspects of the present technology are described below as numbered clauses (1, 2, 3, etc.) for convenience. These are provided as examples and do not limit the subject technology. The features of any of the following Clauses can be combined with features of any of the other Clauses. For example, the features recited in Clause 11 can be combined with the features of any one of the other Clauses listed.

Clause 1. A negative pressure wound therapy system comprising:
a wound dressing; and
a suction device configured to be in fluid communication with the wound dressing via a first conduit to channel a fluid between the wound dressing and the suction device, the suction device comprising:
a vacuum connection configured to be coupled to a second conduit;
a vacuum pump configured to supply negative pressure;
an electronic pressure sensor in electrical communication with the vacuum pump; and
a passive valve assembly in fluid communication with (1) the vacuum pump, (2), the electronic pressure sensor, and (3) the vacuum connection to the wound, wherein the passive valve assembly is configured to maintain the vacuum pump in fluid communication with the vacuum connection within a predefined pressure range, and to passively inhibit fluid communication between the vacuum pump and the vacuum connection outside of the predefined pressure range.

Clause 2. The system of any one of the preceding Clauses, further comprising a canister in fluid communication with both the wound dressing and the vacuum connection of the suction device, wherein the canister is configured to collect exudate aspirated from the wound dressing.

Clause 3. The system of any one of the preceding Clauses, wherein the passive valve assembly comprises:
an interior configured to receive negative pressure from the vacuum pump;
an ambient vent outlet;
a vacuum outlet;
a first moveable occluder configured to close and open the ambient vent outlet with respect to the interior in response to pressure conditions within the interior; and
a second moveable occluder configured to close and open the vacuum outlet with respect to the interior in response to pressure conditions within the interior.

Clause 4. The system of any one of the preceding Clauses, wherein the first movable occluder comprises a first plunger assembly, and wherein the second movable occluder comprises a second plunger assembly.

Clause 5. The system of any one of the preceding Clauses, wherein the passive valve assembly further comprises a sensor outlet in fluid communication with the electronic pressure sensor, wherein the second moveable occluder is configured to close and open the sensor outlet with respect to the interior in response to pressure conditions within the interior, and wherein the electronic pressure controls actuation of the vacuum pump in response to sensed pressure from the sensor outlet.

Clause 6. The system of any one of the preceding Clauses, wherein in the absence of applied negative pressure from the vacuum pump, both the first moveable occluder and the second moveable occluder are closed.

Clause 7. The system of any one of the preceding Clauses, wherein in the presence of negative pressure within the predefined pressure range, the second moveable occluder opens the vacuum outlet with respect to the interior, and the first moveable occluder closes the ambient vent outlet with respect to the interior.

Clause 8. The system of any one of the preceding Clauses, wherein the presence of negative pressure having a greater magnitude than the predefined pressure range, the first moveable occluder opens the vent outlet with respect to the interior.

Clause 9. The system of any one of the preceding Clauses, wherein the first moveable occluder comprises a first spring coupled to a first plunger, and wherein the second moveable occluder comprises a second spring coupled to a second plunger.

Clause 10. The system of any one of the preceding Clauses, wherein the first plunger assembly is more compressed than the second plunger assembly.

Clause 11. The system of any one of the preceding Clauses, wherein the first plunger assembly exerts a greater outward force than the second spring.

Clause 12. The system of any one of the preceding Clauses, wherein the electronic pressure sensor is in analog electronic communication with a circuit network of other analog electronic components and integrated circuits, wherein none of the components are microcontrollers or microprocessors.

Clause 13. The system of any one of the preceding Clauses, wherein the circuit network comprises a logic module that utilizes one or more comparators with hysteresis with an upper threshold and lower threshold within the predefined pressure range.

Clause 14. The system of any one of the preceding Clauses, wherein the vacuum connection comprises:
a male connector secured to the suction device;
a female connector removably coupleable to the male connector; and
a filter disposed between the female connector and the male connector.

Clause 15. The system of any one of the preceding Clauses, wherein the male connector is in fluid communication with the passive valve assembly, and wherein the female connector comprises a connector configured to engage with the second conduit.

Clause 16. The system of any one of the preceding Clauses, wherein the vacuum connection permits the passage of air therethrough, and wherein substantially all air passing through the vacuum connection passes through the filter.

Clause 17. The system of any one of the preceding Clauses, wherein the female connector comprises an engagement mechanism including a first wing coupled to a first barb and a second wing coupled to a second barb, and wherein the male connector comprises an engagement member, the first and second barbs configured to mate with the engagement member to secure the female connector and the male connector together.

Clause 18. The system of any one of the preceding Clauses, wherein inwardly deflecting the first and second wings releases the first and second barbs from the engagement member.

Clause 19. The system of any one of the preceding Clauses, wherein the female connector comprises a receptacle configured to receive the filter therein.

Clause 20. The system of any one of the preceding Clauses, wherein the female connector is sterilizable and reusable.

Clause 21. The system of any one of the preceding Clauses, wherein the canister is nonspecific and is coupled to the device by a mechanism that does not have any moving pieces and does not require a particular waste canister rotational orientation inside the device.

Clause 22. The system of any one of the preceding Clauses, wherein the predefined pressure is −125 mmHg.

Clause 23. The system of any one of the preceding Clauses, wherein the predefined pressure range comprises −125 mmHg plus or minus approximately 10% or less.

Clause 24. The system of any one of the preceding Clauses, wherein the predefined pressure range comprises 125 mmHg plus or minus approximately 20% or less.

Clause 25. The system of any one of the preceding Clauses, wherein the system does not include a microprocessor or microcontroller.

Clause 26. The system of any one of the preceding Clauses, wherein the level of negative pressure created by the suction device is not adjustable by a user.

Clause 27. The system of any one of the preceding Clauses, wherein the vacuum pump comprises a microdiaphragm pump.

Clause 28. A suction device for negative pressure wound therapy, the suction device comprising:

a vacuum connection configured to deliver negative pressure to a treatment site;

a pump configured to supply negative pressure to the vacuum connection; and a passive valve assembly in fluid communication with the pump and the vacuum connection, wherein the passive valve assembly is configured to maintain the pump in fluid communication with the vacuum connection within a predefined pressure range, and to passively inhibit fluid communication between the pump and the vacuum connection outside of the predefined pressure range.

Clause 29. The device of claim 28, further comprising a pressure sensor in electrical communication with the pump; and wherein the pressure sensor is in analog electronic communication with a circuit network of other analog electronic logic components and integrated circuits, where none of the integrated circuits are microcontrollers or microprocessors.

Clause 30. The device of any one of the preceding Clauses, wherein the circuit network comprises a logic module that utilizes one or more comparators with hysteresis with a set point and reset point within the predefined pressure range.

Clause 31. The device of any one of the preceding Clauses, wherein the passive valve assembly comprises:

an interior configured to receive negative pressure from the vacuum pump;

an ambient vent outlet;

a vacuum outlet;

a first moveable occluder configured to close and open the ambient vent outlet with respect to the interior in response to pressure conditions within the interior; and a second moveable occluder configured to close and open the vacuum outlet.

Clause 32. The device of any one of the preceding Clauses, wherein the passive valve assembly further comprises a sensor outlet; and wherein the second moveable occluder is additionally configured to close and open the sensor outlet with respect to the interior in response to pressure conditions within the interior.

Clause 33. The device of any one of the preceding Clauses, wherein in the absence of applied negative pressure from the pump, both the first moveable occluder and the second moveable occluder are closed.

Clause 34. The device of any one of the preceding Clauses, wherein in the presence of negative pressure within the predefined pressure range, the second moveable occluder opens the vacuum outlet with respect to the interior, and the first moveable occluder closes the ambient vent outlet with respect to the interior.

Clause 35. The device of any one of the preceding Clauses, wherein the presence of negative pressure having a greater magnitude than the predefined pressure range, the first moveable occluder opens the vent outlet with respect to the interior.

Clause 36. The device of any one of the preceding Clauses, wherein the vacuum connection comprises:

a male connector secured to the suction device;

a female connector removably coupleable to the male connector; and a filter disposed between the female connector and the male connector.

Clause 37. The device of any one of the preceding Clauses, wherein the male connector is in fluid communication with the passive valve assembly, and wherein the female connector comprises a connector configured to engage with a conduit.

Clause 38. The device of any one of the preceding Clauses, wherein the vacuum connection permits the passage of air therethrough, and wherein substantially all air passing through the vacuum connection passes through the filter.

Clause 39. The device of any one of the preceding Clauses, wherein the female connector comprises an engagement mechanism including a first wing coupled to a first barb and a second wing coupled to a second barb, and wherein the male connector comprises an engagement member, the first and second barbs configured to mate with the engagement member to secure the female connector and the male connector together.

Clause 40. The device of any one of the preceding Clauses, wherein inwardly deflecting the first and second wings releases the first and second barbs from the engagement member.

Clause 41. The device of any one of the preceding Clauses, wherein the female connector comprises a receptacle configured to receive the filter therein.

Clause 42. The device of any one of the preceding Clauses, wherein the female connector is sterilizable and reusable.

Clause 43. The device of any one of the preceding Clauses, further comprising a waste canister configured to be coupled to a conduit without moving pieces, the device configured to accommodate non-specific waste canisters in different rotational positions.

Clause 44. The device of any one of the preceding Clauses, wherein the predefined pressure range includes −125 mmHg.

Clause 45. The device of any one of the preceding Clauses, wherein the device does not include a microprocessor or microcontroller.

Clause 46. The device of any one of the preceding Clauses, wherein the predefined pressure range is not adjustable by a user.

Clause 47. The device of any one of the preceding Clauses, wherein the pump comprises a microdiaphragm pump.

Clause 48. A method of applying negative pressure wound therapy, the method comprising:

(a) disposing a wound dressing over a wound site on a patient;

(b) fluidically coupling the wound dressing to a canister;

(c) fluidically coupling the canister to a suction device, thereby establishing a fluidic pathway;

(d) supplying power to the suction device;

(e) determining pressure in the fluidic pathway using a pressure sensor;

(f) comparing the pressure to an upper threshold and a lower threshold;

(g) powering on a pump of the suction device until the pressure meets the upper threshold;

(h) after (g), powering off the pump until the pressure falls to the lower threshold;

(i) repeating steps (e)-(h) to maintain pressure in the fluidic pathway between the upper threshold and the lower threshold; and (j) terminating therapy by removing power to the suction device and relieving pressure in the fluidic pathway.

Clause 49. The method of any one of the preceding Clauses, further comprising:

(k) fluidically connecting the pressure sensor to a passive valve assembly, wherein the passive valve assembly comprises:

an interior configured to receive negative pressure from the pump;

an ambient vent outlet;

a vacuum outlet;

a sensor outlet;

a first moveable occluder configured to close and open the ambient vent outlet with respect to the interior in response to pressure conditions within the interior; and a second moveable occluder configured to close and open the vacuum outlet with respect to the interior in response to pressure conditions within the interior;

(l) limiting the maximum vacuum pressure in the fluidic pathway with the passive valve assembly; and (m) preventing backflow in the fluidic pathway.

Clause 50. The method of any one of the preceding Clauses, wherein the upper threshold is between 5 and 15% greater than a therapeutic vacuum level for therapy, and wherein the lower threshold is between 5 and 15% lower than the therapeutic vacuum level for therapy.

Clause 51. The method of any one of the preceding Clauses, further comprising providing a first indication signifying that the pressure is lower than specified for therapy while the pressure is rising until the pressure reaches the upper threshold.

Clause 52. The method of any one of the preceding Clauses, further comprising providing a second indication signifying that the pressure is within a therapeutic range while the pressure is falling until the pressure reaches the lower threshold.

Clause 53. The method of any one of the preceding Clauses, wherein a maximum rate of state change between the first indicator and another indicator is between 0.5 and 2 Hz.

Clause 54. The method of any one of the preceding Clauses, wherein the center of a range bounded by the upper threshold and the lower threshold is 125 mmHg.

Clause 55. The method of any one of the preceding Clauses, wherein the upper and lower thresholds are not configurable by a user.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 4E is a table of the different operating conditions of the suction device.

DETAILED DESCRIPTION

Selected Embodiments of Negative Pressure Wound Therapy Systems

Figure 1A:
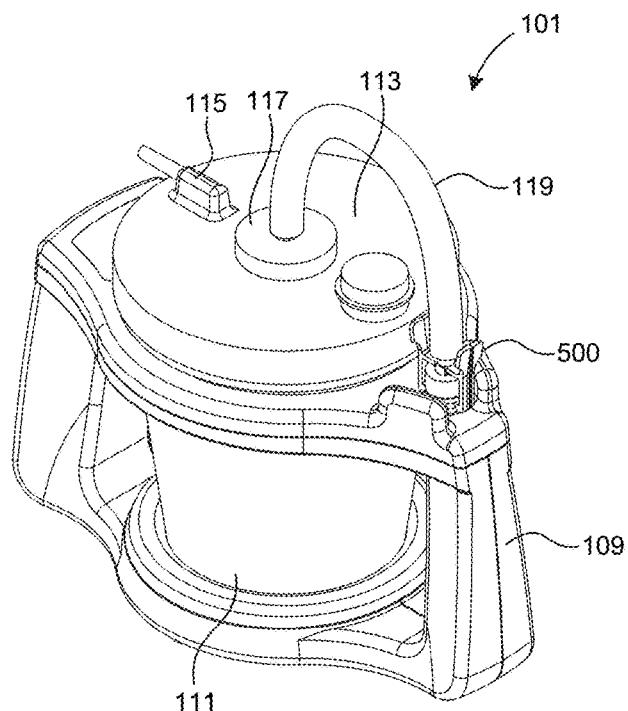
FIG. 1A is a perspective view of a suction assembly of a negative pressure wound therapy (NPWT) system in accordance with an embodiment of the present technology.

FIG. 1A is a perspective view of a suction device 101 of a negative pressure wound therapy (NPWT) system 100 in accordance with an embodiment of the present technology, and includes a housing 109, a conduit 119, and a connection assembly 500. The housing contains mechanical and electrical components that are further described in FIGS. 2A-C. FIG. 1A shows the suction device 101 coupled with a canister 111 and lid 113. The lid 113 further comprises an exudate port 115 and a vacuum port 117.

Figure 1B:
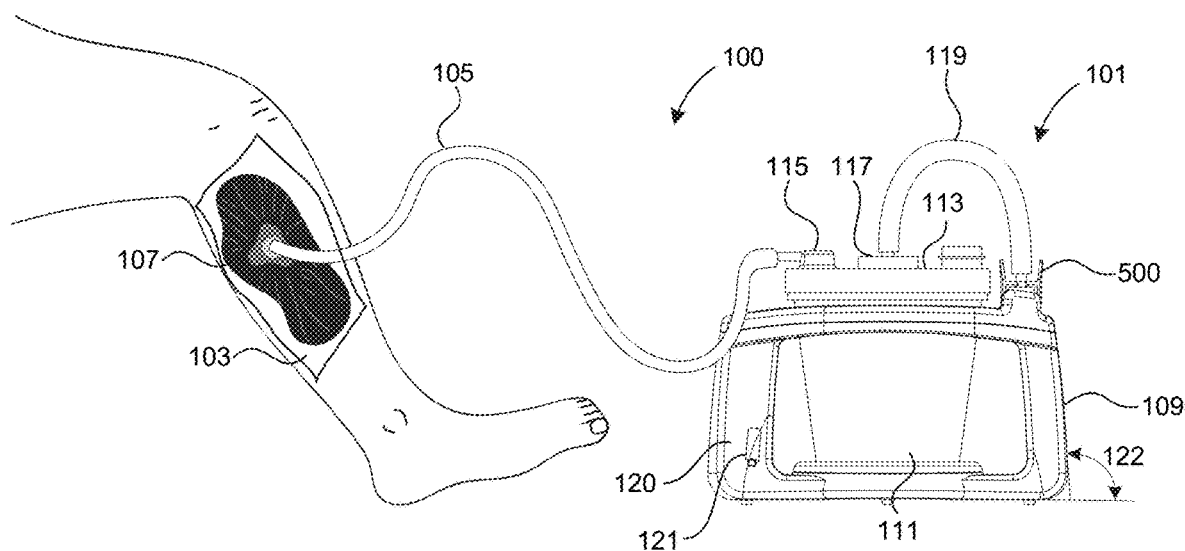
FIG. 1B illustrates the NPWT system positioned to treat a wound on a patient's leg.

FIG. 1B illustrates the NPWT system 100 positioned to treat a wound on a patient's leg. The NPWT system 100 includes the suction device 101, a canister 111, a lid 113, a dressing 103, and a conduit 105 configured to couple the suction device 101 to the dressing 103. As described herein, the system 100 is preferably configured to treat a wound by application of reduced pressure to a wound site 107 (i.e., below atmospheric pressure) to provide suction to the wound site 107 in a controlled manner for a desired period of time.

Figure 1C:
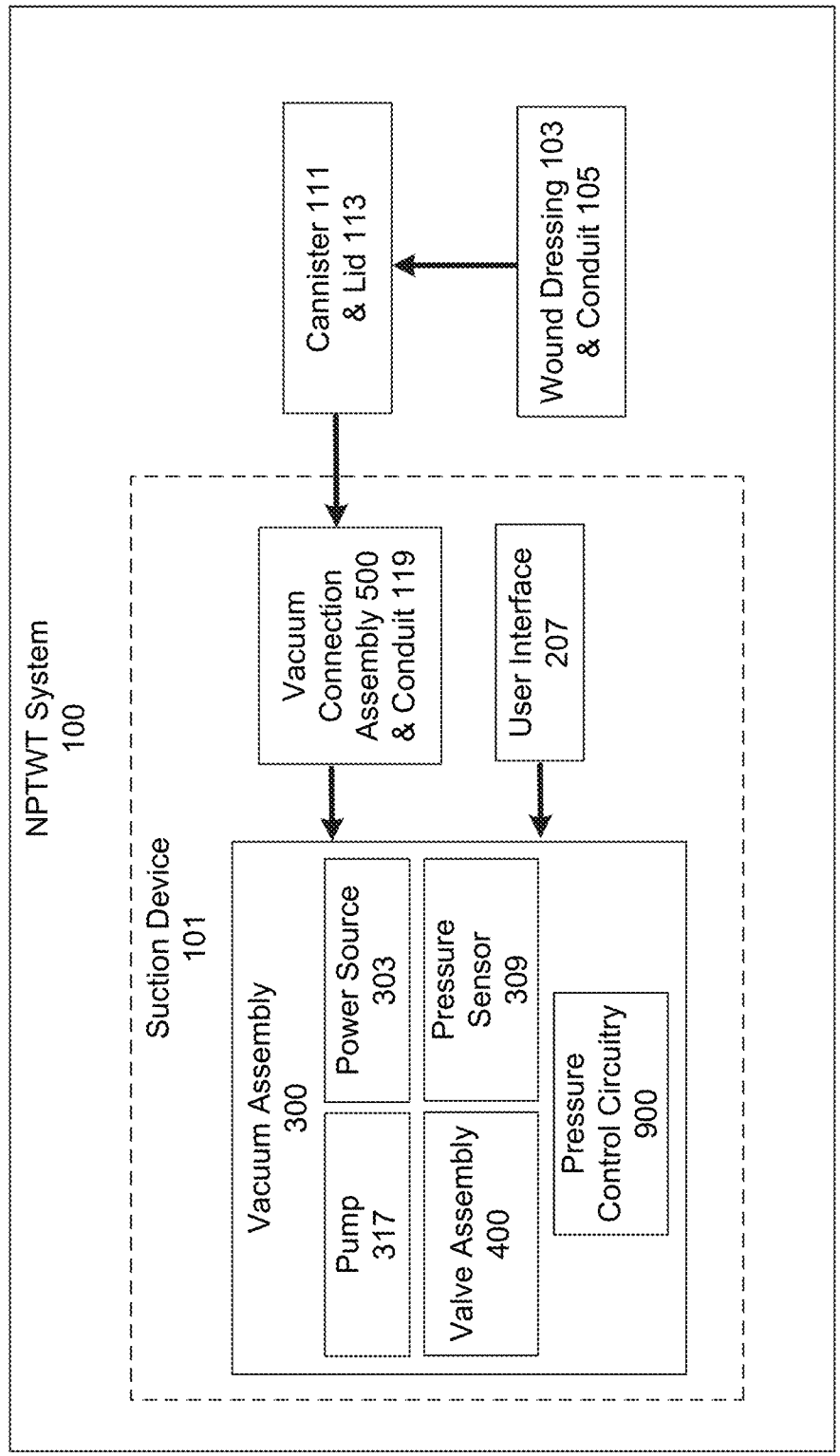
FIG. 1C illustrates a schematic view of the NPWT system of FIGS. 1A and 1B.

FIG. 1C illustrates a schematic view of the NPWT system 100 of FIGS. 1A and 1B. The system 100 includes the suction device 101 in communication with the wound dressing 103 and canister 111. Specifically, the wound dressing is in communication with the cannister 111 (e.g., via a conduit), and the cannister 111 in turn is in fluid communication with a vacuum assembly 300 via a connection assembly 500. Embodiments of the connection assembly 500 are described in more detail below with respect to FIGS. 5A-5C. The vacuum assembly 300, described in more detail below with respect to FIGS. 2A-4G, can include a pump 317, a power source 303, a pressure sensor 309, pressure control circuitry 700, and a valve assembly 400. Together, these components of the vacuum assembly 300 can provide a supply of negative pressure within a desired therapeutic range to the wound dressing 103 via the connection assembly 500 and the cannister 111. The vacuum assembly may be in electrical communication with the user interface 207. In some embodiments, the suction device 101 can be enclosed within a housing or other body.

The dressing 103 can be a wound cover or wound dressing configured to enclose the wound site 107 and to provide a fluid-tight or gas-tight enclosure over the wound site 107 to effect treatment of a wound site 107 with reduced or negative pressure. Any wound cover or dressing presently known in the art or developed in the future can be configured to be integrated into the NPWT system 100 described herein.

To create suction within the dressing 103, the dressing 103 is connected to the suction device 101 via the conduit 105. The suction device 101 provides a source of suction to deliver reduced pressure for the sealed wound dressing 103 at the wound site 107. As described in more detail below, the suction device 101 includes a housing 109 which encompasses a vacuum assembly that supplies negative pressure. In some embodiments, all electronic components and pneumatic system parts are contained within the housing 109. The housing 109 defines an opening configured to receive a canister 111 therein. The canister 111 can be configured to hold exudate that is aspirated from the wound site 107. The canister 111 can be covered with a lid 113 that includes an exudate port 115 and a vacuum port 117. The exudate port 115 is configured to be coupled to the conduit 105 that extends between the suction device 101 and the dressing 103. The vacuum port 117 can be coupled to a conduit 119 that is coupled to a connection assembly 500 which in turn is coupled to the housing 109 of the suction device 101. In use, negative pressure is supplied through the connection assembly 500, through the conduit 119, and to the vacuum port 117 such that negative pressure is provided within the canister 111. Since the canister 111 is open to the exudate port 115, the negative pressure within the canister 111 creates negative pressure within the conduit 105 and therefore negative pressure at the wound site 107 under the dressing 103. The application of negative pressure causes exudate to be aspirated from the wound site 107. The exudate passes through the conduit 105, through the exudate port 115, and into the canister 111 where it is collected for later disposal.

As described in more detail below with respect to FIGS. 5A-5C, the female connector 501 of the vacuum connection assembly 500 can be easily connected and disconnected from the male connector 503 of the vacuum connection assembly 500 for the purpose of removing the canister 111 temporarily from the suction device 101 in order to dispose of exudate build-up in the canister, cleaning the housing 109, or to replace disposable components of the suction unit such as the connection assembly 500 itself and canister 111. The male connector 503 can be permanently bonded to the housing 109 (e.g. with adhesive or ultrasonic welding) or semi-permanently attached to the housing 109 (e.g. with plastic screw threads). The ease of connecting and disconnecting the female connector 501 from the housing ensures safety by allowing a non-skilled user to interrupt the vacuum connection to the patient if needed. This easily repeatable process to secure an airtight seal between the male connector 503 and female connector 501 also reduces the risk of air-leak related performance failures.

Figure 2A:
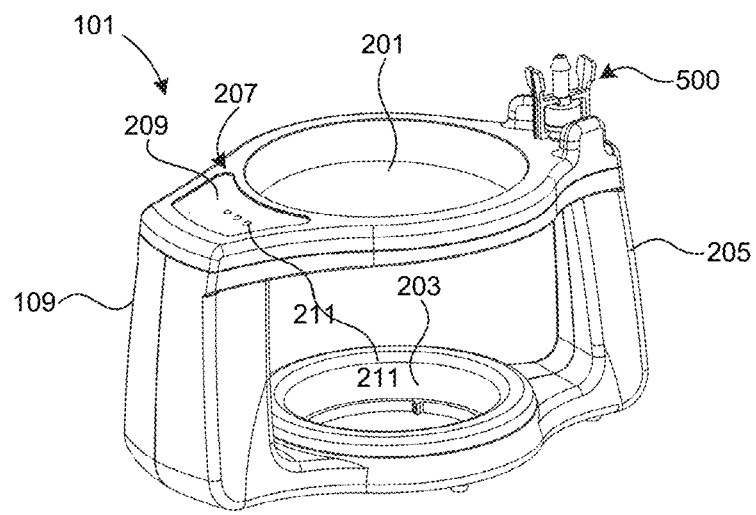
FIG. 2A illustrates a perspective view of a suction device in accordance with embodiments of the present technology.
Figure 2B:
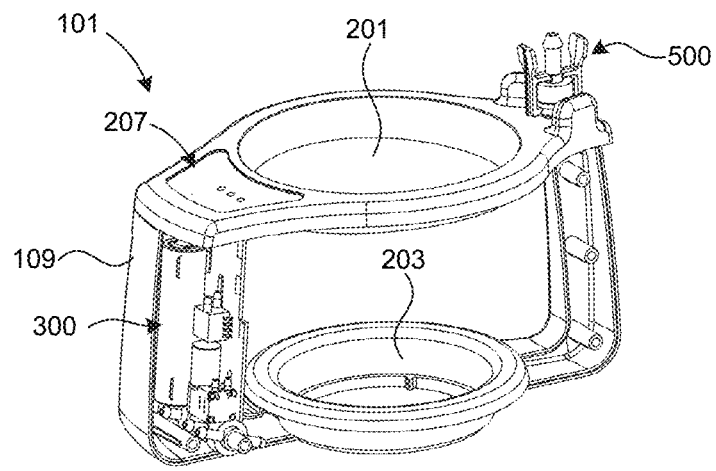
FIG. 2B illustrates the suction device system of FIG. 2A with a portion of the housing removed.

FIG. 2A illustrates the suction device 101 with the conduit 119, omitted, and FIG. 2B illustrates the suction device 101 of FIG. 2A with a portion of the housing 109 removed to reveal interior features. Referring to FIGS. 2A and 2B together, the housing 109 is shaped and configured to encompass interior components of the suction device 101, including a vacuum assembly 300, a connection assembly 500, and interior conduits connecting components of the vacuum assembly 300 and connection assembly 500 for operation (conduits not shown for clarity).

Figure 8:
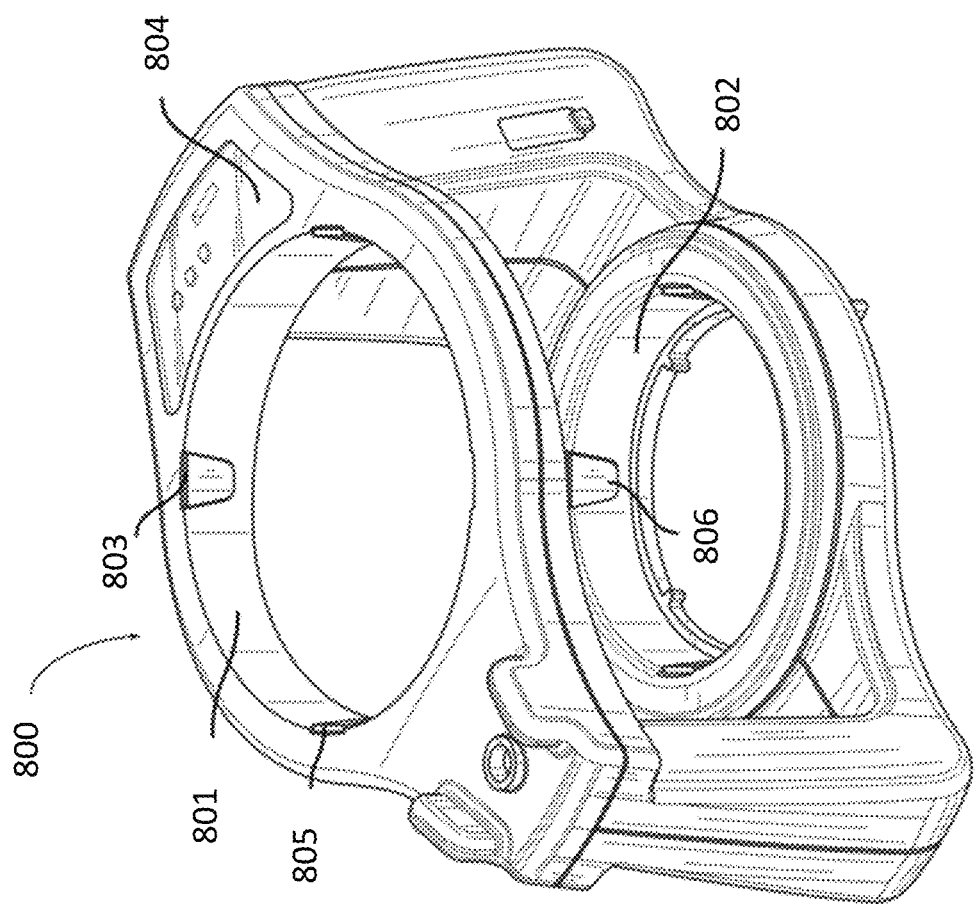
FIG. 8 illustrates another embodiment of a suction device.

The housing 109 forms an upper aperture 201 and a lower ring 203 (FIG. 2A) that are together configured to receive a canister 111 (FIGS. 1A and 1B) therein. The shape of the suction device 101 allows a large canister 111 to be used with the device. In some embodiments, the cannister 111 can be a container configured to collect greater than 300 ml wound exudate for the treatment of chronic wounds with high fluid output (e.g. 300 ml-800 ml). In contrast, conventional portable/disposable NPWT systems are typically volume-limited (e.g. 70-300 ml) and cannot treat highly exuding wounds. The diameters of the upper aperture 201 and lower ring 203 permits the use of standard, market available containers, with both appropriate tubing connections and a smooth tapered form, to be paired with the suction device 101. This could permit users to employ the most available and/or cost-effective option from a selection of containers, whereas conventional wound vacuum products are typically designed to only work with custom or internal collection containers, so customers have no choice in collection container and may not be able to replace the container when it becomes full. Additionally, as shown in FIG. 8, which illustrates another embodiment of a suction device 800, the upper aperture 801 and lower ring 802 may contain securement pads 803, 805, 806 to establish a friction fit between the canister 111 and housing 109. In some embodiments the securement pads 803, 805, 806 are adhesive foam pads or silicone pads. This enables a standard canister to be held in place without the use of latches or other moving mechanisms. This housing 109 shape and simple canister securement mechanism described above additionally allows for the canister contents to be easily seen from different positions during use, which helps patients, doctors or caregivers notice and respond to changes such as the color of the fluid or the rate of fluid collection in the canister. The canister 111 may be secured in any rotational position desired to facilitate treatment.

The housing 109 also forms a pair of ergonomic handles 205, 120 that allow a user to grip the suction device 101 during operation with one or two hands. The shape of the housing 109 allows the suction device 101 to be carried comfortably by caregivers or patient, or to be passed between people. Additionally, the construction is both highly portable and very stable when in use. In some embodiments, the housing 109 can have an overall length along its longest axis of between about 7-14 inches, a height of between about 5-9 inches, and a width that varies from about 1 inch (at the handle) to 7 inches (at the canister) and 3 inches (at the electronics compartment 120). Several aspects of the housing 109 can be configured for portability, including handle dimensioning, handle tilt, and device weight. With respect to handle dimensioning, a standardized handle for typical hand sizes can be used. With respect to handle tilt, by orienting the handle 205 on the device with an angle such as angle 122 shown in FIG. 1, in a range of 95 to 110 degrees, a user is able to carry the device easily while ensuring that the suction device remains upright. In some embodiments, the weight of the device can be between about 1-10 lbs to ensure that a single person can transport the device with ease. The weight range is based on conservative, established limits for the intended user population. For example, the general recommended limit for lifted weights by Humanscale 4/5/6 is 22 lbs for women over 50 years of age. The overall device volume can be small enough for easy transport, and in some embodiments a carrying case can also be used.

In some embodiments, aspects of the housing 109 can be configured specifically for improved stability. For example, a low center of gravity and ballast at the base (provided by the canister fluid) ensure bottom-heavy stability. The base surface of the housing 109 can be provided with rubber feet, suction cups, or other high-friction elements to increase grip between the lower surface of the housing 109 and the base surface. In some embodiments, the surface area of the lower surface of the housing 109 can be greater than the surface area of a top surface of the housing 109, such that the housing tapers inwardly from the bottom to the top, thereby providing a relatively wide base to improve stability of the device when resting on a surface.

Figure 2C:
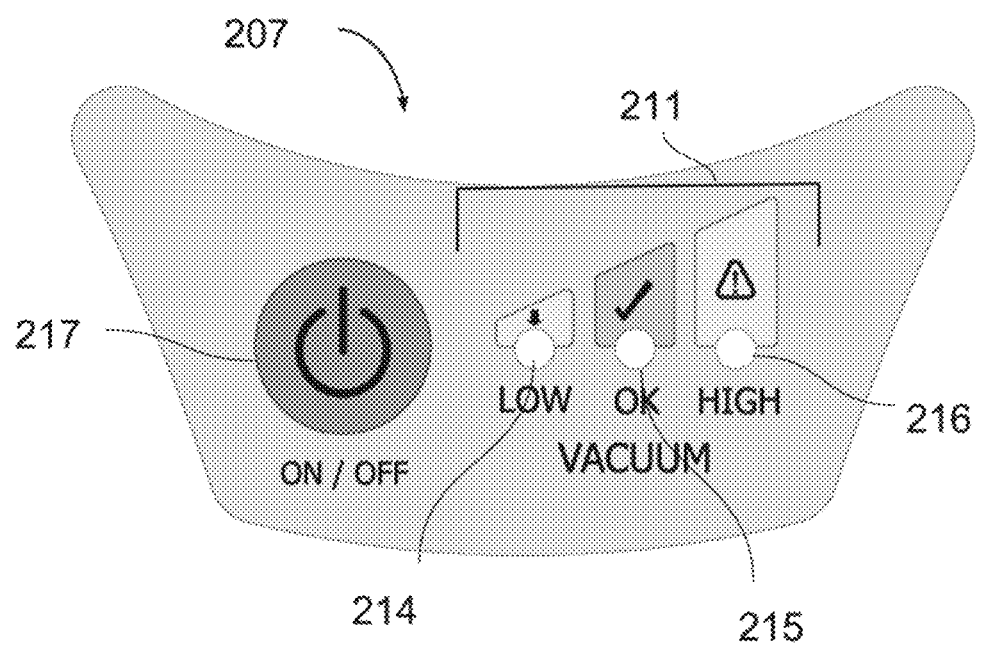
FIG. 2C illustrates a user interface of the suction device shown in FIGS. 2A and 2B.

FIG. 2C illustrates a user interface 207 that is provided on an upper surface of the housing 109 on the side opposite the handle 205. The user interface 207 can include one or more indicators 211 combined with symbols, markings or letters, for example, indicators of battery level, device operation, error messages, etc. In some embodiments, the indicators at the user interface 207 can be lights (e.g., LEDs 214, 215, 216), foregoing the need for more complex and expensive screen-based displays or touch-screen interfaces. The user interface 207 can also include a power (on/off) button 217 and a charging port 121, shown in FIG. 1B, for one or more standard power inputs.

FIG. 2B shows the vacuum assembly 300 that provides the source of negative pressure and is fluidically coupled to the connection assembly 500 via internal conduits (not shown). FIGS. 1A and 1B illustrate how the connection assembly 500, is in turn coupled to the lid 113 via a conduit such as 119 to the vacuum port 117.

Selected Embodiments of Vacuum Assemblies

Figure 3:
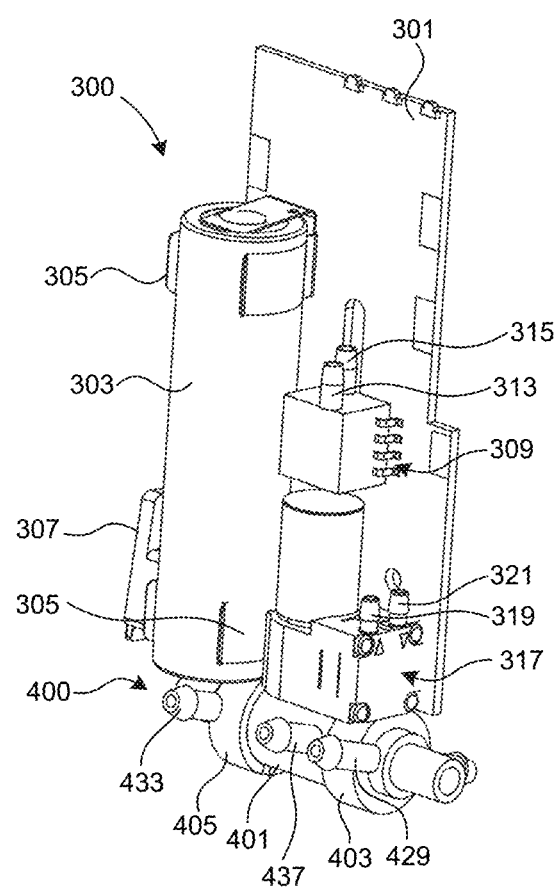
FIG. 3 is an enlarged view of the pump assembly of the suction device shown in FIGS. 2A and 2B.

FIG. 3 is an enlarged view of the vacuum assembly 300 shown in FIG. 2B. The vacuum assembly 300 provides the source of negative pressure and includes a printed circuit board (PCB) 301 or other substrate onto which various components can be mounted. A power source 303 (e.g., a battery) is mounted to the PCB 301 and secured in place via one or more clips 305. In some embodiments, the power source 303 is a rechargeable lithium-ion or other suitable battery. A charging adapter 307 is mounted to the PCB 301 and configured to engage an electrical cable (not shown) that connects to the charging port 121, shown in FIG. 1B, of the suction device 101 and to the power source 303.

In at least some embodiments, the suction device 101 has low power requirements and low current draw. For example, in some embodiments the suction device 101 can run on less than 6V, less than 5V, or less than 4V. This low power requirement can be achieved by, among other things, eliminating the need for a microcontroller with the pressure control circuitry 700, shown in FIG. 7, using a low-power pump (such as a microdiaphragm pump), and omitting a screen-based display interface in favor of a simplified user interface 207. One benefit of this lower power need is that the device can be powered by, for example, a 5V DC power source and does not require constant AC wall power.

As shown in FIG. 3, a sensor 309 is mounted to the PCB 301 to detect the pressure. In some embodiments, the sensor includes an atmospheric input connector 313 that is exposed to the ambient air and a sensor input connector 315. This allows for the device to be used at different elevations as the vacuum level prescribed for therapy is relative to ambient. The connectors 313 and 315 can be barbed connectors configured to receive tubing thereover. In other embodiments, any other suitable connectors can be used. The ambient connector 313 can be unconnected to any tubing, and open to the ambient air within the housing 109. As described in more detail below, the sensor input connector 315 can be connected to the valve assembly 400 via a conduit (not shown) to detect the pressure within the valve assembly 400. The sensor 309 can be in indirect electrical communication with a pump 317 through electronic components configured to cause the pump to be turned on and off in response to sensor outputs. In use, the sensor input connector 315 is coupled to the valve assembly 400 as described in more detail below. In at least some embodiments, the pressure sensed via the sensor input connector 315 is translated into a voltage that scales (e.g., linearly) with vacuum pressure within a predetermined range (e.g., 0-250 mmHg, 50-180 mmHg). This voltage becomes an input to pressure control circuitry 700 to determine whether it falls outside of a predetermined threshold (e.g. target pressure of 80 mmHg, 125 mmHg or 180 mmHg with a tolerance of 5, 10, 15 or 20%) and if the pump or other indicators should be activated or inactivated.

Figure 6:
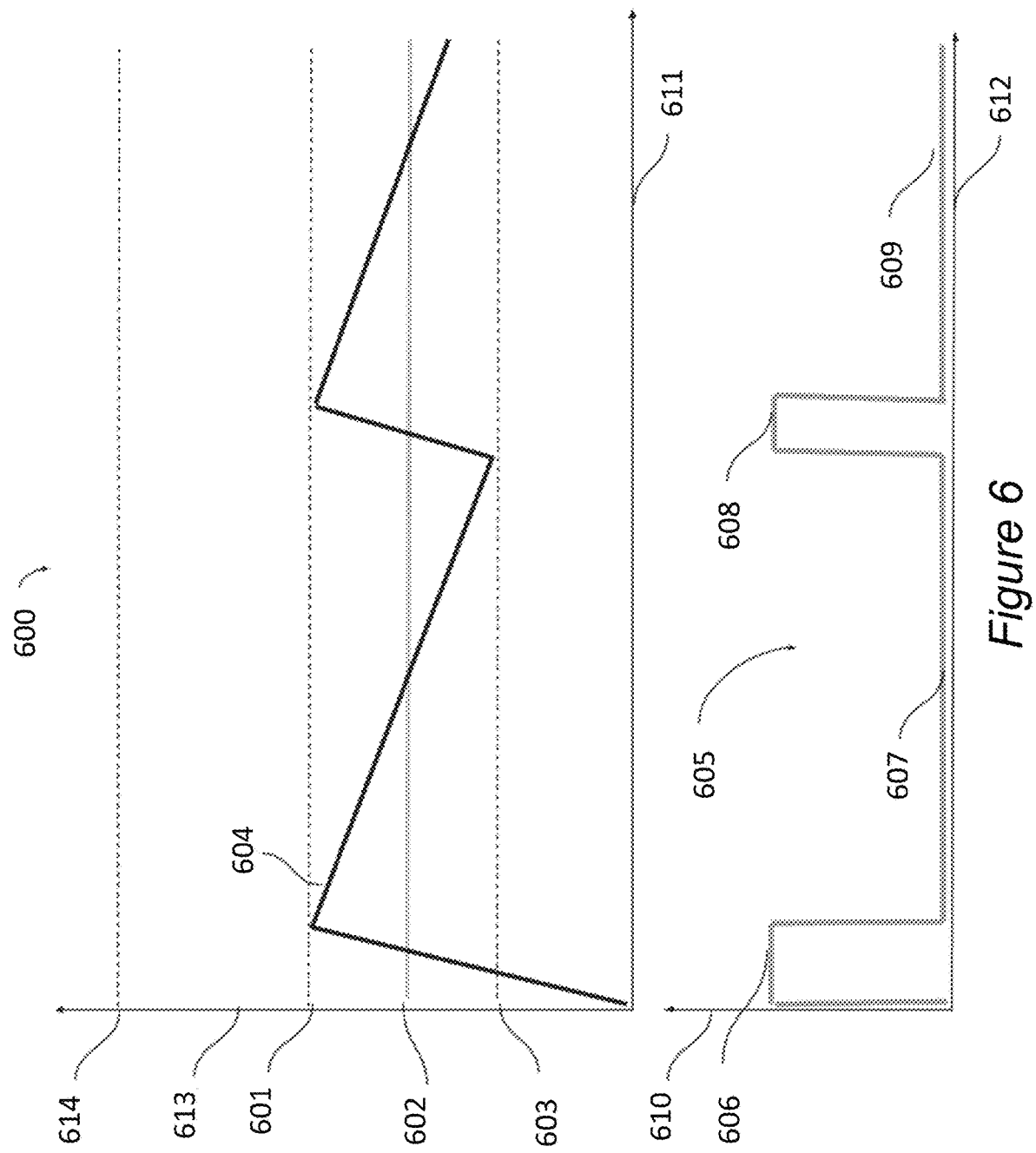
FIG. 6 shows graphs of vacuum pressure and pump voltage over time.
Figure 7:
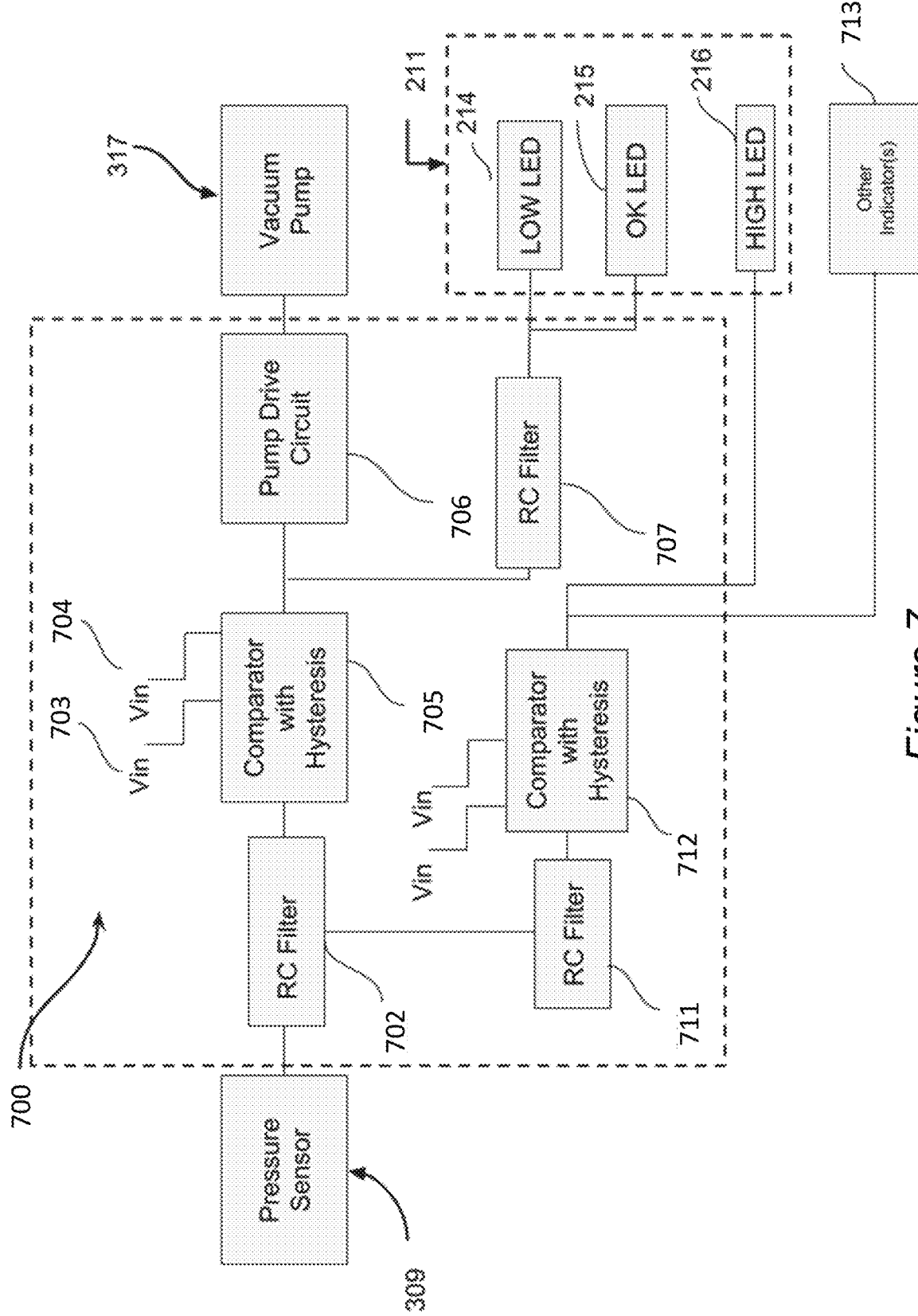
FIG. 7 is a schematic diagram of pressure control circuitry of a suction device.

Mounted on the PCB 301 may be electronic components including the pressure control circuitry 700, which is shown in FIG. 7. This circuitry may include comparators 705, 712, RC filters 702, 707, 711, a pump motor drive circuit or chip 706 and may not include microcontrollers or microprocessors. The circuitry is not controlled by on-device software of any kind. The first RC filter 702 filters the sensor 309 output. The output of the filter is analyzed by a first comparator with hysteresis 705. The first RC filter 702 may have a time constant of 0.05 to 0.5 milliseconds, which serves to filter out any noise from being delivered to the comparator and to also limit the pump maximum rate of state change from on to off or from off to on. The output of the first comparator with hysteresis is electrically connected to the pump drive circuit 706 which is connected to the vacuum pump 317. The output of the first comparator with hysteresis 705 is additionally connected to a RC filter 707 which may have a time constant of 0.5 to 2 seconds. The output of this filter may be connected to LEDs 214, 215. The function of this RC filter 707 is to limit the maximum rate of state change of the LEDs 214, 215 such that a viewer is not confused and the LEDs do not appear to flicker. The output of the first RC filter 702 is also connected to a third RC filter 711 with a time constant of 0.5 to 2 milliseconds. The output of this RC filter 711 is interpreted by a second comparator with hysteresis 712. The function of the third RC filter 711 is to additionally remove noise from the input to the second comparator with hysteresis 712 and control the maximum rate of state change in the output of the second comparator with hysteresis 712. The output of this second comparator is electrically connected to a LED 216 and may be connected to other indicators 713 such as an audio alarm, and/or additional LEDs. The detailed mechanisms of this pressure control circuitry and how they interact with other elements of the suction device 101 to control pressure for NPWT are explained in greater detail along with the description of FIG. 6 in a later section. The circuitry 700 serves to maintain system vacuum pressure within a therapeutic range with an upper threshold (e.g. a value between 130 and 150 mmHg) and lower threshold (e.g. a value between 100 and 120 mmHg) by selectively actuating the pump 317 in response to sensed vacuum pressure levels. In some embodiments, fixed passive components like resistors and capacitors set the upper and lower thresholds for vacuum pressure control in this system. In other embodiments, these inputs may be variable, such as a potentiometer used instead of a resistor, which would allow for the device's upper and lower thresholds 601, 603 (as shown in FIG. 6) to be adjustable during manufacturing or by service technicians. The selective actuation of the pump 317 is achieved without using microcontrollers or microprocessors, which reduces the cost and complexity of the system as compared to conventional systems that rely on microprocessor-based pump control schemes.

The LEDs 214, 215, 216 of the user interface (UI) 207 are driven by outputs of the pressure control circuitry 700. The function of the RC filter 707 is to slow the state change rate between LED 214 and LED 215 when the pressure sensed is near the upper threshold value or lower threshold value. This avoids flickering between the two states of LOW pressure and OK pressure to not confuse an end user who may believe that the two states are occurring simultaneously if the state change rate is too rapid. 0.5 to 2 Hz has been determined experimentally to be the ideal state change rate for these UI elements. The LED 216 is driven by the second comparator with hysteresis 712. Like the first comparator 705, this component can be configured with passive components like resistors and capacitors to give a selective output when the vacuum pressure is sensed to be greater than a particular value which may be higher than the upper threshold. The output may be activating the LED 216 to signal danger to a user and additionally activating other indicators 713 which may be audio alarms or other LEDs.

In some embodiments, the PCB 301 also includes one or more of the following sensors: a temperature sensor for the monitoring of temperature of the air; a current sensor to monitor current drawn by different parts of the system; a flow rate sensor to monitor flow rate and detect any blockage issues in the pneumatic system; a gyroscope to monitor orientation of the suction unit to reduce the risk of tilt and potential fluid spillage; a global positioning system (GSP) to monitor device location; a biosensor to detect signs of infection in the fluid; or a humistor to detect environmental humidity levels that may affect device performance. Various other sensors can be incorporated onto the PCB 301 or otherwise coupled to the vacuum assembly 300.

With continued reference to FIG. 3, the pump 317 is also mounted to the PCB 301. The pump 317 includes a vacuum output connector 321 and an exhaust connector 319. The connectors 319 and 321 can be barbed connectors configured to receive tubing thereover. In other embodiments, any other suitable connectors can be used. The exhaust connector 319 can be unconnected to any tubing, and open to the ambient air within the housing 109 to vent exhaust from the pump 317. As described in more detail below, the vacuum output connector 321 can be coupled to the connector 437 of the valve assembly 400 to provide negative pressure.

The pump 317 can be, for example, a microdiaphragm pump. In at least some embodiments, a significant cost reduction is achieved by selecting an inexpensive pump. This also reduces the power requirement for the system. For example, in at least some embodiments the pump 317 can run off less than 5V of power, for example approximately 3.3V. In some embodiments, the pump 317 can have a lower flow rate than conventional NPWT devices, which typically operate in the range of 1.5-10 L/minute. In some embodiments, the flow rate can be less than 1 L/minute, for example approximately 0.7 L/minute. The low flow rate of the pump 317 allows for delivery of a specific vacuum pressure to the wound site while using a simple control method with only analog electronic components (which is also very low cost). Because each stroke of the pump moves a small volume of air with respect to the total system air volume, the system is not at risk of overshooting the target pressure with a simple DC square wave bang-bang control. This obviates the need for a solenoid valve or microprocessor to correct the vacuum pressure because of the above-mentioned resolution from a low flow rate pump and a large air reservoir (provided via the canister 111). Such low-flow pumps have an additional benefit over the higher flow pumps used in conventional NPWT systems in that they are low cost, small, and lightweight. Use of a lower flow rate pump may extend the user's wait time to establish a therapeutic vacuum level when the system is being initially depressurized, but once a therapeutic vacuum level is established, the low flow rate pump does not affect therapy safety or effectiveness. Current NPWT disposables are not able to use such a simple control mechanism because their reservoirs are too small (70-300 mL), so the system pressure must be monitored and controlled more actively, e.g. by use of an electromechanical bleed valve.

Various aspects of the present technology can allow for the use of an inexpensive pump, which is a benefit in reducing device production cost without compromising therapy quality or safety:
1) Method of Pressure Control: As described above, the valve system suggested when used in combination with the control circuitry described in FIGS. 6 and 7, allows for the pump 317 to be actuated selectively (i.e. turn on/off) to maintain negative pressure within a predetermined threshold, rather than requiring the pump 317 to run continuously. In at least some embodiments, a pump with less efficiency (e.g., brush motor instead of brushless), fixed speeds and lower duty cycle ratings or reduced longevity (e.g. rated life, hours of continuous use) can be utilized in the suction device 101, as compared to the pumps utilized in most stand-alone devices.
2) Single Pressure Setting: Providing negative pressure at a predefined, single-setting set point enables the use of a pump 317 that is narrowly specified for most efficient performance in the therapeutic range. Therefore, the device can utilize a pump that is rated to a threshold just above the nominal vacuum pressure level (e.g., in some embodiments for example, the pump only has to achieve 125 mmHg+/−10% of vacuum, such that a pump that is rated up to 180 mmHg vacuum is sufficient whereas a pump rated up to 250 mmHg vacuum would be unnecessary).
3) Flow Rate Requirements: Embodiments of the described NPWT technology do not require high-flow rates to deliver the vacuum pressure required for therapy. In fact, a low-flow rate allows high resolution in delivery of a specific vacuum pressure to the wound site while using a simple control method with only analog electronic components (which is also very low cost). Therefore, the pump provided in the system does not require a high-flow rate.
4) The Pump Specifications: a) lower duty cycle requirements, b) lower quality requirements, c) lower pressure rating requirements, d) lower flow rate requirements each enable the use of an inexpensive pump to be utilized in the NPWT suction device. In some embodiments, the pump can be, for example, a microdiaphragm pump, a pump technology that with specifications that meet the requirements of the NPWT technology herein described, and a low cost, can provide significant cost savings when utilized.

In currently-marketed NPWT devices, in combination with a microprocessor or microcontroller, a solenoid valve may be actuated to release vacuum pressure in a controlled manner in the instance when the device determines the pressure is "too-high" or the pressure setting is reduced (e.g., negative pressure set-point is decreased and/or pressure cycle is intermittent or variable such that the pressure is increases and decreasing on a cycle that needs to be reliably controlled). Various aspects of the present technology allow for the device, in some embodiments, to omit any requirement for a solenoid valve to control pressure:
1) Single Setting Pressure: The therapeutic vacuum level can be predetermined, making user-controlled pressure settings a nonfactor and eliminating the requirement for a solenoid valve to release vacuum pressure for the purpose of adjusting the nominal vacuum pressure to meet user inputs.
2) No intermittent or variable pressure: In some embodiments, vacuum pressure is not increased or decreased on a cycle, and is instead reliably controlled within a threshold of the predefined therapeutic level, also omitting the requirement for a solenoid valve to release vacuum pressure accordingly.
3) Mechanical Release Valve: In the instance when the pressure is "too-high," a passive (non-powered) mechanical release valve can be used that opens in response to high vacuum pressure in the system, replacing the need for a powered solenoid valve.

Figure 4A:
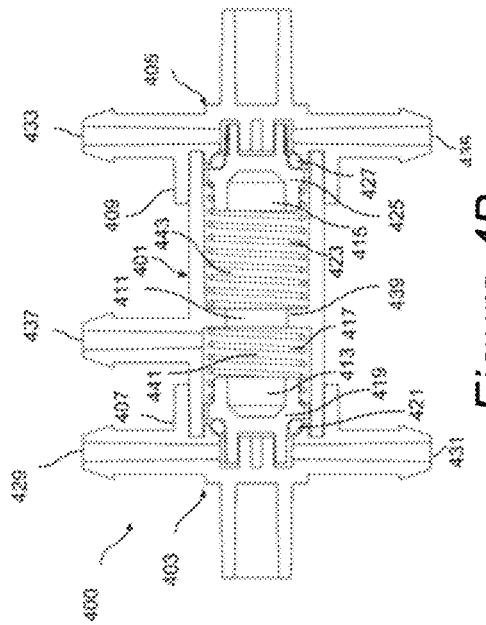
FIG. 4A illustrates a perspective view of the valve assembly shown in FIG. 3.
Figure 4B:
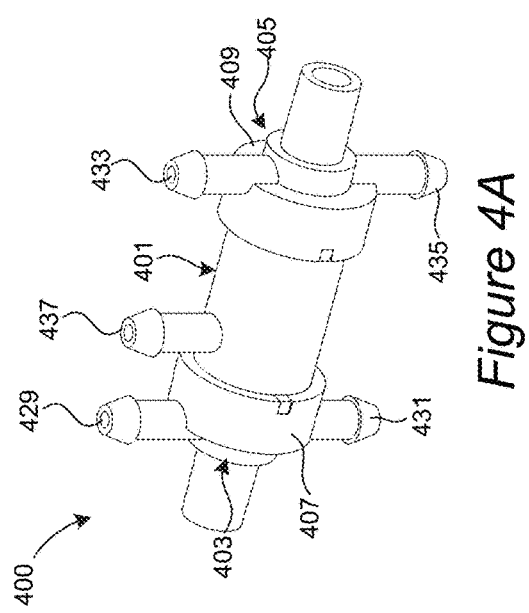
FIG. 4B illustrates a side cross-sectional view of the valve assembly of FIG. 4A.
Figure 4C:
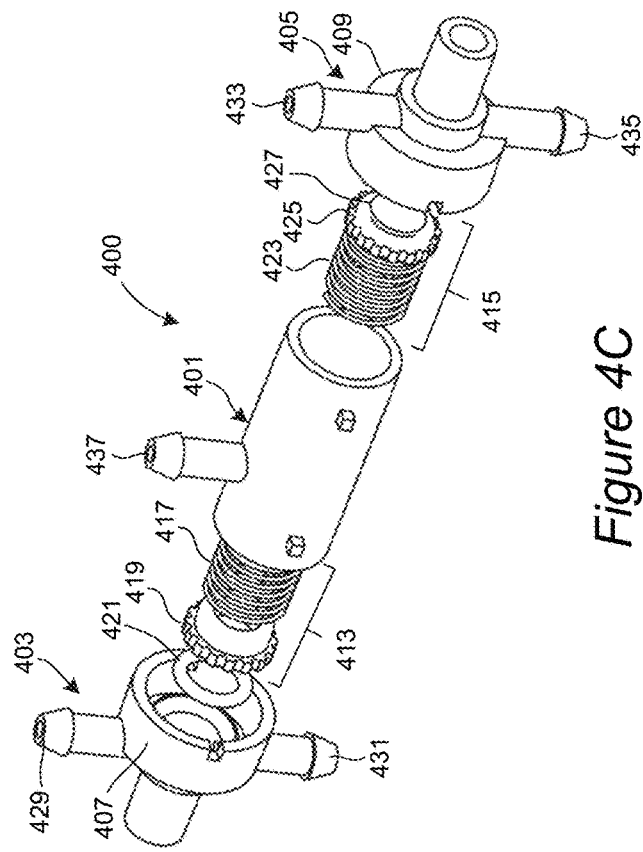
FIG. 4C illustrates a perspective exploded view of the valve assembly of FIGS. 4A and 3B.

As shown in FIG. 3, a valve assembly 400 is disposed adjacent to the PCB 301 and is connected to the sensor 309 and pump 317 as described in more detail below. FIGS. 4A-4C are enlarged detailed views of the valve assembly 400. In particular, FIGS. 4A-4C illustrate a perspective, cross-sectional, and perspective exploded views, respectively, of the valve assembly 400 shown in FIG. 3. Referring to FIGS. 3-4C together, the valve assembly 400 is a mechanical relief valve that interfaces between the pump 317 and the connection assembly 500 which supplies negative pressure to the cannister 111 and to the wound site 107 (FIG. 1B). Conventional NPWT systems often use solenoid valves to regulate delivery of negative pressure to the wound site. Solenoid valves are expensive and require precise microcontroller actuation. In contrast, and as noted above, embodiments of the present technology provide a passive mechanical valve assembly 400 that is low-cost and may be used with sensor 309 and electronic circuitry 700 on the PCB 301 to maintain applied pressure in the therapeutic range. In at least some embodiments, the valve assembly 400 combines the functions of a check valve and an over-pressure release valve. The check valve ensures that flow through the system occurs in only a single direction, preventing exudate from ever flowing backwards into the suction device 101. The over-pressure release valve is designed to release pressure when it exceeds a predetermined value based on the unique design. In some cases the over-pressure release valve will release pressure when the pressure exceeds 150 mmHg or any other pressure value greater than 150 mmHg. This also enables the device to regulate pressure electrically, such that no initial or periodic tuning by hand or mechanical monitoring by users is required to maintain appropriate pressure for effective NPWT. In some embodiments, no user intervention is required to maintain the appropriate set-point pressure (e.g., physical adjustments and/or tuning to the device). In some conventional NPWT devices, periodic adjustments and manual user intervention, for example tuning a pressure dial coupled with a bleed valve or alternatively, software-enabled electromechanical controls to adjust pressure, are required to ensure pressure is regulated. These design features significantly reduce the complexity of the system and vastly improves the ease of use.

The valve assembly 400 can include a generally cylindrical body 401 with first and second end caps 403 and 405 disposed on opposing sides. The end caps 403 and 405 can have cylindrical portions 407 and 409 configured to receive portions of the body 401 therein. When the end caps 403 and 405 are fitted over the ends of the cylindrical body 401, they together define an interior space 411. Within the interior space are disposed a first plunger assembly 413 and a second plunger assembly 415. The first plunger assembly 413 can include a first spring 417, a first plunger 419, and a first O-ring 421. The second plunger assembly 415 can include a second spring 423, a second plunger 425, and a second O-ring 427. As described in more detail below, the first and second plunger assemblies 413, 415 serve as moveable occluders, which can each move between an "open" position in which air is permitted to pass through a corresponding aperture and a "closed" position in which air is inhibited from flowing through the aperture. Although some embodiments disclosed herein use plunger assemblies as moveable occluders, in other embodiments alternative structural arrangements can be used, for example bellows, diaphragms, etc.

The body 401 and end caps 403 and 405 can include one or more protruding connectors, each of which are configured to receive a conduit (e.g., plastic tubing) thereon to provide fluidic connection for air to flow from the interior space 411 through interior lumens of the connectors. The connectors can be barbed connectors configured to receive tubing thereover. In other embodiments, any other suitable connector type can be used. The first end cap 403 includes first and second ambient vent connectors 429 and 431. When the first plunger assembly 413 does not occlude flow from the interior 411 through these ambient vent connectors 429 and 431, ambient air is permitted to pass through these connectors 429 and 431.

The second end cap 405 includes a sensor output connector 433 and a vacuum output connector 435. The sensor output connector 433 is configured to be coupled via a conduit (e.g., plastic tubing) to the sensor input connector 315 of the pressure sensor 309. The vacuum output connector 435 is configured to be coupled via a conduit (e.g., plastic tubing) to the connection assembly 500 to deliver negative pressure to the wound site 107. When the second plunger assembly 415 does not occlude flow from the interior 411 to these connectors 433 and 435, negative pressure from the interior 411 is supplied to both to the pressure sensor 309 via the sensor output connector 433, and to the connection assembly 500 via the vacuum output connector 435.

The body 401 includes a vacuum input connector 437 configured to be fluidically coupled via a conduit (e.g., plastic tubing) to the vacuum output connector 319 of the pump 317. In use, negative pressure supplied by the pump 317 is delivered to the interior 411 of the vacuum assembly 400 via the vacuum input connector 437. The body 401 can further include an interior wall 439 that separates the interior 411 into first and second portions 441 and 443. The first portion 441 retains the first plunger assembly 413 therein, and the second portion 443 retains the second plunger assembly 415 therein. The wall 439 can include an opening or aperture so that the first and second portions 441 and 443 are in fluid communication with one another. In some embodiments, the wall 439 provides a surface against which the springs 417 and 423 of the respective plunger assemblies 413 and 415 can press. The first portion 441 can be smaller than the second portion 443, such that the wall 439 is positioned off-center with respect to the body 401.

In at least some embodiments, the first and second plunger assemblies 413 and 415 can be constructed from similar components. For example, the first spring 417 and the second spring 423 can have similar constructions, with similar or identical spring constants (e.g., having a spring constant suitable to generate forces needed to open or close the coupling to a conduit at a clinically-relevant pressure for wound therapy), uncompressed sizes (e.g., having an uncompressed length of between about 0.5 cm and about 5 cm), material composition, etc. Similarly, the first and second plungers 419 and 425 and the first and second O-rings 421 and 427 can be made of similar or identical materials with similar or identical sizes and configurations. In operation, the first O-ring 421 can engage with an outer surface of the first plunger 419, and the first spring 417 can be disposed adjacent to the first plunger 419. The first spring 417 can be configured to exert an outward force on the first plunger 419. In use, the first spring 417, with one end positioned against the wall 439, exerts an outward force on the first plunger 419 such that the first plunger 419 and first O-ring 421 together abut against the first end cap 403. In this position, the first plunger 419 and first O-ring 421 occlude the flow of air between the interior 411 and the first and second ambient vent connectors 429 and 431 of the first end cap 403.

Similarly, the second spring 423, positioned against the wall 439, exerts an outward force on the second plunger 425 such that the second plunger 425 and the second O-ring 427 together abut against the second end cap 405. In this closed position, the second plunger 425 and the second O-ring 427 occlude the flow of air between the interior 411 and both the sensor output connector 433 and the vacuum output connector 435 of the second end cap 405.

In the absence of any applied negative pressure, the first and second plunger assemblies 413 and 415 can remain in the closed configurations (as illustrated in FIG. 4B), in which the interior 411 is not open to either the first or second ambient vent connectors 429 and 431 of the first end cap 403, or to the sensor output connector 433 or the vacuum output connector 435 of the second end cap 405. As negative pressure is applied to the interior 411 via the vacuum input connector 437, the first and second plungers 421 and 425 can be urged inwardly toward the wall 439, and if sufficient negative pressure is applied, this inward urging of the first and second plungers 421 and 425 can overcome the outward force of the first and second springs 417 and 423. In at least some embodiments, the first spring 417 exerts a greater outward force on the first plunger 421 than force exerted by the second spring 423 on the second plunger 427. As a result, as negative pressure increases above a certain threshold within the interior 411, the inward urging of the second plunger 427 will overcome the outward force of the second spring 423, however the inward urging of the first plunger 421 will not be sufficient to overcome the outward force of the first spring 417. In this configuration, the first plunger assembly 413 remains in the closed configuration, while the second plunger assembly 415 will be pulled into the open configuration. This permits the interior 411 to be in fluid communication with the sensor output connector 433 and the vacuum output connector 435 of the second end cap 405. Negative pressure is therefore delivered from the pump 317, through the valve assembly 400, and out to both the connection assembly 500 (via the vacuum output connector 435) and to the sensor 309 (via the sensor output connector 433). As noted above, pressure detected at the sensor 309 can be used to selectively actuate the pump 317, thereby permitting the pump 317 to be run only when required to achieve the desired pressure. In the presence of any positive pressure (e.g., urging air flow from the direction of the vacuum assembly 400 towards the connection assembly 500, rather than the reverse), both the first and second plunger assemblies 413 and 415 will be urged into the closed position. The thresholds of pressure required to move either or both of the first and second plunger assemblies can be modified by use of springs with greater or lesser spring constants, or springs with greater or lesser length.

As negative pressure within the interior 411 increases, the first plunger 421 can be urged inward with sufficient force to overcome the outward force of the first spring 413, thereby causing the first plunger assembly 413 to assume the open configuration. In this configuration, the interior 411 is open to the first and second ambient vent connectors 429 and 431, which will cause ambient air to enter the interior 411 until the pressure has risen to a level such that the first plunger assembly 413 returns to the closed configuration. As a result, the first plunger assembly 413 can serve as an over pressure release valve, in which excess negative pressure is relieved by opening the valve assembly 400 to ambient air (via the first and second ambient vent connectors 429 and 431).

The pump 317, the position of the wall 439, the plunger assemblies 413, and 415, and the sensor 309 can all be configured to achieve a desired negative pressure delivered to the patient. Advantageously, this therapeutic vacuum level range (e.g., in some embodiments about 125 mmHg+/−10%) can be selected and controlled during manufacturing and assembly, and does not require user input or modification of the device to achieve the therapeutically effective negative pressure. For example, this pressure range can be controlled during manufacturing with simple changes in components, component sizing and length, component material, choice of connection point configuration, number of components used (multiple springs), or addition of spacers or reducers. In at least some embodiments, the user cannot modify the amount of negative pressure supplied via the device 101. In some embodiments, the vacuum assembly 400 allows the suction device 101 to supply negative pressure only within a predetermined range. In some embodiments, the pump 317, valve assembly 400, and sensor 309 are all configured such that the negative pressure delivered to the patient can be approximately −125 mmHg, plus or minus 10%. If the pressure drops below this predetermined threshold (i.e., a higher magnitude of negative pressure), the first plunger assembly 413 opens to vent ambient air, and if the pressure rises above this predetermined threshold (i.e., a smaller magnitude of negative pressure), the second plunger assembly 415 closes, the sensor 309 detects the change, and the pump 317 can be restarted.

As noted above, the first spring 417 can exert a greater outward force than the second spring 423. In the illustrated embodiment, this can be achieved by utilizing substantially identical springs that have been compressed to different degrees due to the off-center position of the wall 439. In other embodiments, the differential outward force of the springs can be achieved by using springs with different spring constants or other constructions such that the first spring 417 exerts a greater outward force than the second spring 423, irrespective of the position of the wall 429. Additionally, in certain embodiments the springs 417 and 423 can be replaced with other resilient members (e.g., balloons, elastomeric members, bellows, etc.) configured to exert an axially outward force on the plungers 419 and 425. FIG. 4E illustrates the different conditions that may exist in the use of the embodiment described above and how this embodiment responds to the conditions. Conditions 1 and 2 listed in FIG. 4E may occur simultaneously. Conditions 1 and 4 may also occur simultaneously. Conditions 3 and 4 may also occur simultaneously. Conditions 2 and 3 may not occur simultaneously in the embodiment described by FIGS. 4B and 4C.

Figure 4D:
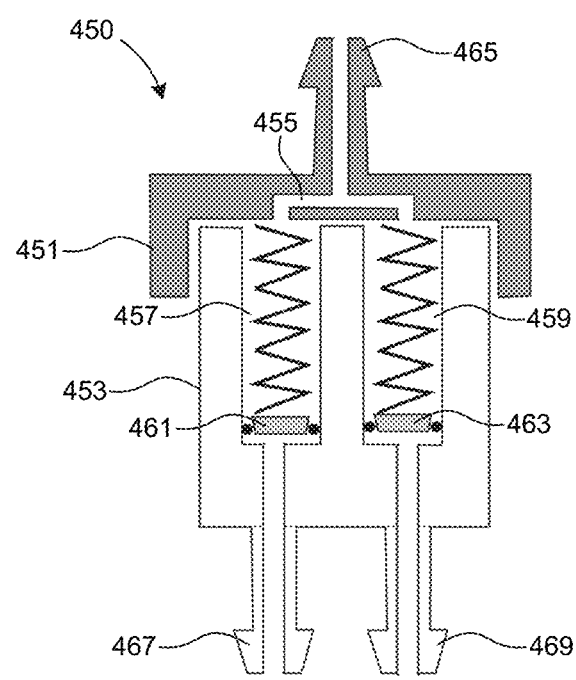
FIG. 4D illustrates another embodiment of a valve assembly.
Figure 4F:
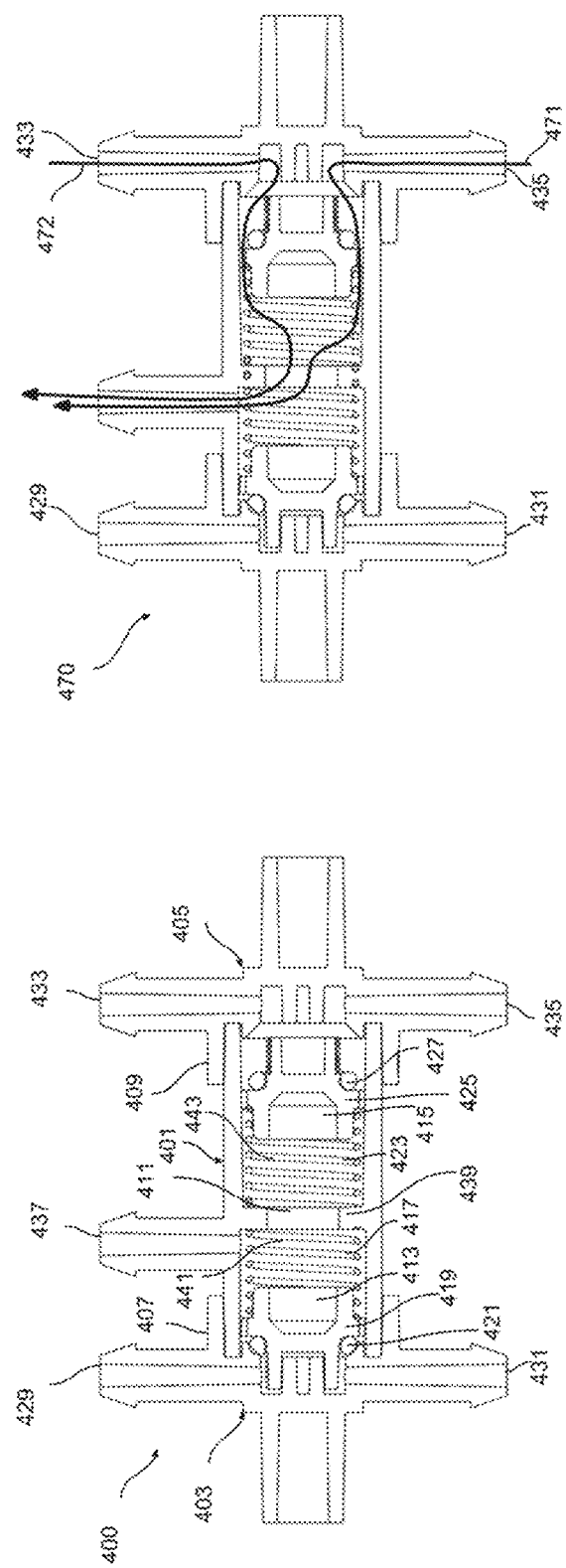
FIGS. 4F and 4G illustrate how the valve assembly responds to changes in relative pressure.
Figure 4G:
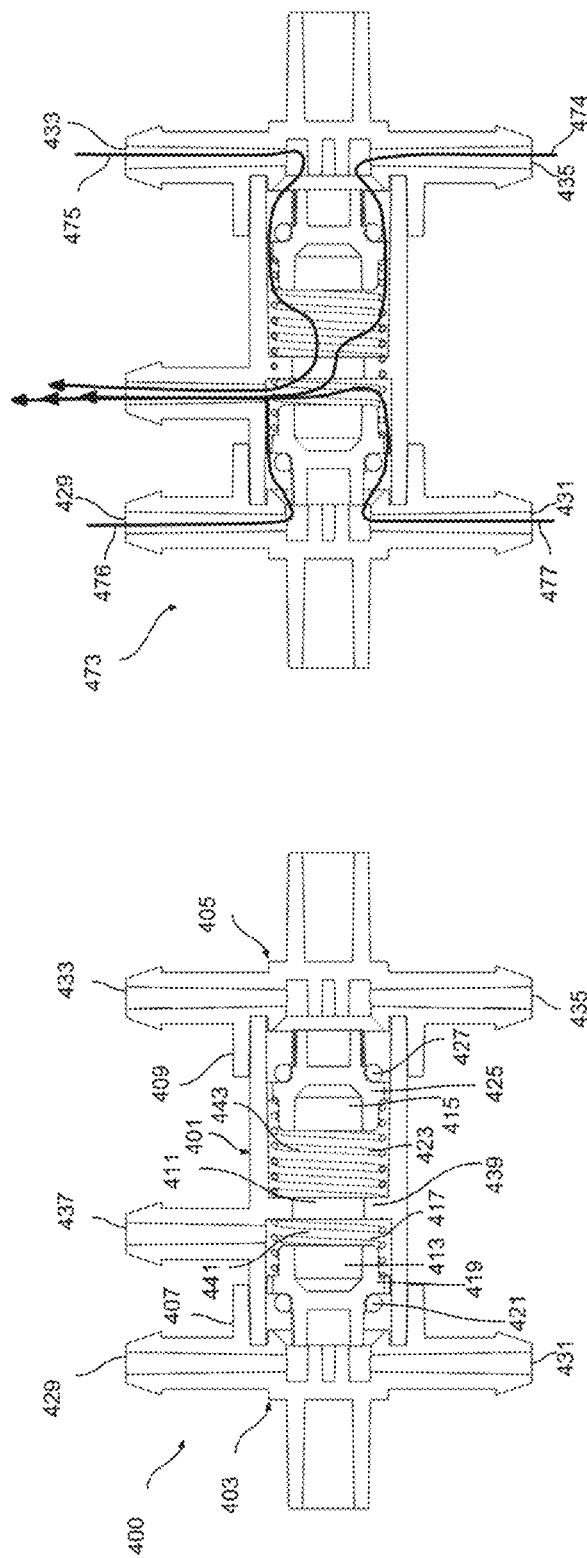

FIGS. 4F and 4G illustrate how the passive valve assembly 400 and plunger assemblies 413, 415 respond to changes in relative pressure in the system. FIG. 4B illustrates the "fully closed" state of the assembly 400, which is a combination of Conditions 3 and 4 (FIG. 4E) in which both plunger assemblies 413, 415 are in the "closed" position. FIG. 4F illustrates the combination of Condition 1 and 4 (FIG. 4E) wherein the plunger assembly 415 is in the "open" position and plunger assembly 413 is in the "closed" position. Configuration 470 of the shown in FIG. 4F is illustrated with lines 472 and 471 showing how air can flow through the assembly 400, from connectors 433 and 435 into connector 437 when in this state. FIG. 4G illustrates the combination of Condition 1 and 2 (from FIG. 4E) wherein both plunger assemblies 413 and 415 are in the "open" positions. Configuration 473 shown in FIG. 4G is illustrated with lines 474, 475, 476 and 477 representing how air can flow through the assembly 400 from connectors 433, 435, 431 and 429 around the plunger assemblies in "open" positions and into connector 437.

The valve assembly 400 can take a variety of others forms while providing the functionality of a combined over-pressure release valve and a check valve. For example, FIG. 4D illustrates another embodiment of a valve assembly 450 that can serve as both an over-pressure release valve and a check valve. The assembly 450 includes a first body 451 mated with a second body 453 to define an interior chamber 455. The chamber 455 includes first barrel 457 and second barrel 459 which house first and second moveable occluders 461 and 463, respectively. The moveable occluders can take the form of plunger assemblies as described above (e.g., plungers coupled to springs). In other embodiments, the moveable occluders can include bellows, diaphragms, or other mechanisms to moveably occlude flow through the respective barrels of the chamber 455. Each of the moveable occluders 461, 463 is moveable between a "closed" configuration in which air flow through its respective barrel is blocked and an "open" configuration in which air flow through its respective barrel is permitted. For example, with respect to the first moveable occluder 461, the "closed" position can be achieved when the occluding surface (e.g., the plunger at the end of the spring) is in contact with a lower wall of the first barrel 457, thereby occluding flow between the ambient vent connector 467 and the first barrel 457. The "open" position can be achieved when the occluding surface is separated from the lower wall of the first barrel 457 (e.g., by compression of the spring to move the occluding surface away from the lower wall of the first barrel 457). In this open configuration, the first barrel 457 is in fluid communication with the ambient vent connector 467. Similarly, the second moveable occluder 463 can be moved between a closed configuration in which the second barrel 459 is not in fluid communication with the vacuum output connector 469 and an open configuration in which the second barrel 459 is in fluid communication between the second barrel 459 and the vacuum output connector 469. The moveable occluders 461 and 463 can be configured such that they move from open to closed configurations under different conditions, such as at different negative pressure thresholds, as described in more detail below.

The chamber 455 is in fluid communication with three connectors: a pump input connector 465, an ambient vent connector 467, and a vacuum output connector 469. In use, the pump input connector 465 is coupled (e.g., via a conduit) to the pump 317 which supplies negative pressure. The ambient vent connector 467 is open to the ambient air, and the vacuum output connector 469 is coupled to the canister (e.g., via the connection assembly 500) and can also be coupled to a sensor to provide feedback to the pump.

During operation, negative pressure provided from the pump through the pump input connector 465 is supplied to the chamber 455. The negative pressure within the chamber 455 exerts a compressive force on each of the moveable occluders 461 and 463 which urges them towards their respective open positions. Each of the first and second moveable occluders 461 and 463 can move from the closed to open positions once the supplied negative pressure exceeds a corresponding threshold. In some embodiments, the threshold negative pressure to move the first moveable occluder 461 from the closed to the open state is higher than the corresponding threshold negative pressure required to move the second moveable occluder 463 from the closed state to the open state.

When the supplied negative pressure is less than the threshold for either occluder 461 or 463 (or when there is no negative pressure supplied at all), both moveable occluders 461 and 463 maintain the closed state, and there is no fluid communication between the pump input connector 465 and either the ambient vent connector 467 or the vacuum output connector 469. When the negative pressure supplied is greater than the threshold of the second moveable occluder 463, but lower than the threshold of the first moveable occluder 461, the second moveable occluder 463 maintains the open state while the first moveable occluder 461 maintains the closed state. In this configuration, negative pressure is supplied to the chamber 455 and, via the vacuum output connector 469, to the canister and/or the sensor. If the negative pressure rises to meet or exceed the threshold of the first moveable occluder 461, then the first moveable occluder 461 also moves into the open state. In this state, ambient air is in fluid communication with the chamber 455 via the ambient vent connector 467, and the pressure will in the chamber 455 will rise (i.e., the magnitude of negative pressure will decrease). This provides an over-pressure release function, in which excess negative pressure is "vented" to maintain the negative pressure supplied to the canister within a desired range.

Selected Embodiments of Vacuum Connection Assemblies

Figures 5A, 5B, 5C:
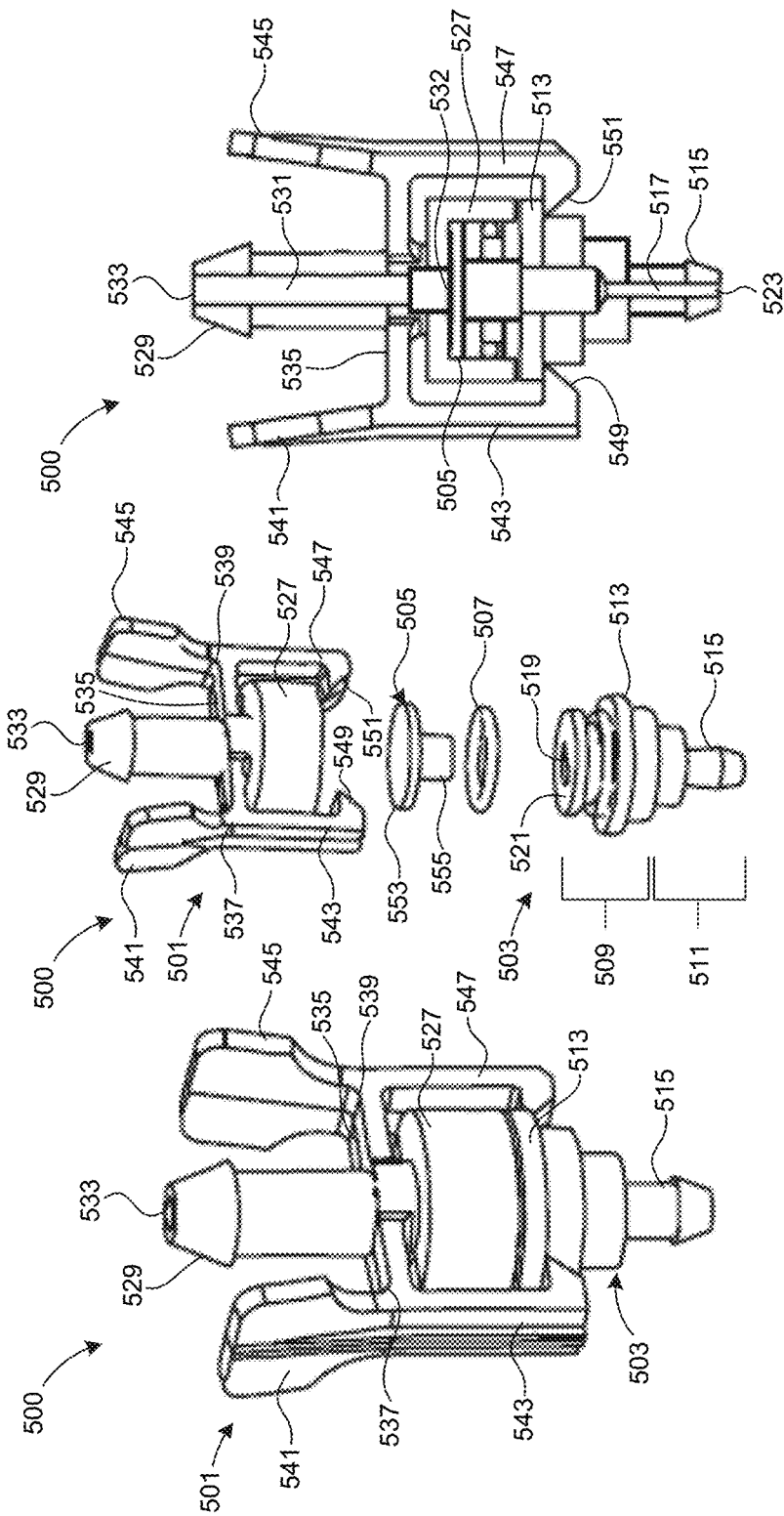
FIG. 5A is an enlarged perspective view of the vacuum connection assembly shown in FIGS. 2A and 2B.
FIG. 5B is an exploded perspective view of the vacuum connection assembly shown in FIG. 5A.
FIG. 5C is a side cross-sectional view of the vacuum connection assembly shown in FIGS. 5A and 5B.

FIGS. 5A-5C are enlarged perspective, exploded perspective, and cross-sectional views, respectively, of the connection assembly 500. As noted above, most conventional wound vacuum products are designed to only work with custom or internal collection containers, so customers have no choice in collection container and may not be able to replace the container when it becomes full. Embodiments of the present technology can allow users to provide their own collection containers for use with the suction device 101 by virtue of the connection assembly 500. The connection assembly 500 enables connection to a generic canister while protecting the suction device 101 from contamination, thereby ensuring patient safety. This also allows for the use of reusable canisters in therapy which reduces medical waste. Particularly in resource-constrained settings such as the developing world, there is great desire to reuse medical equipment wherever possible. The connection assembly 500 allows this to be achieved while maintaining patient and equipment safety. In at least some embodiments, the suction device 101 can be provided with no container, which allows customers to provide a container that has been sterilized or cleaned at the treatment site or elsewhere and possibly used multiple times. In some embodiments, the container need not be sterile at all if the device is sufficiently protected by the connection assembly, particularly with use of a filter as described in more detail below.

The connection assembly 500 can include a female connector 501 that releasably engages a male connector 503. A filter 505 and O-ring 507 can be configured to be received at the junction between the female connector 501 and the male connector 503. In some embodiments, the male connector 503 is configured to be received permanently or semi-permanently within an aperture in the housing (shown as 807 in FIG. 8) such that an upper portion 509 of the male connector 503 protrudes above an upper surface of the housing 109, while the lower portion 511 is positioned within an interior of the housing 109. The upper portion 509 of the male connector 503 can include an engagement member 513 which protrudes radially outwardly from the upper portion 509 and provides a surface against which the female connector 501 can engage, as described in more detail below. The engagement member 513 can be a ring or other shape that permits the female connector 501 to removably engage with the male connector 503.

The lower portion 511 of the male connector 503 can include a downwardly projecting connector 515. In some embodiments, the first lumen 517 extends through the male connector 503 between a first opening 519 on an upper surface 521 of the male connector 503, and a second opening 523 at the end of the connector 515. The connector 515 can be configured to removably engage with a conduit (e.g., plastic tubing), which connects the connection assembly 500 to the vacuum output connector 435 of the valve assembly 400. The intervening conduit (not shown) can extend within the housing 109 between the two connectors.

The female connector 501 can include a receptacle 527 configured to receive a filter 505 and O-ring 507 therein, which allow for the protection of the device from odors or vapors and sealing of the system from ambient leaks. In some embodiments, the receptacle 527 can define a substantially cylindrical opening, though other shapes may be employed in other embodiments. The female connector 501 can additionally include an upwardly extending connector 529. A second lumen 531 extends between a third opening 532 on an interior surface of the receptacle 527 and a fourth opening 533 at the end of the connector 529. The connector 529 is configured to be removably engaged with a conduit (e.g., plastic tubing), which connects the connection assembly 500 to the vacuum port 117 of the lid 113 (FIGS. 1A and 1B).

The female connector 501 can also include a bridge 535 that extends laterally away from the connector 529 in opposing directions, terminating in a first end 537 and a second end 539. At the first end 537, a first wing 541 extends upwardly and a first barb 543 extends downwardly. The first wing 541 and the first barb 543 can be continuous such that manually deflecting the wing 541 inwardly (i.e., towards the connector 529) causes the first barb 543 to deflect outwardly. Similarly, at the second end 539 of the bridge 535, a second wing 545 extends upwardly and a second barb 547 extends downwardly. The barbs 543 and 547 include respective angled protrusions 549 and 551 that project inwardly from the lower ends of the respective barbs 543 and 547. These angled surfaces of these protrusions 549 and 551 are configured such that when the female connector 501 is lowered onto the male connector 503, the angled surfaces of the protrusions 549 and 551 contact the engagement member 513 of the male connector 503. As the female connector 501 is lowered further with respect to the male connector 503, the protrusions 549 and 551 are deflected outwardly to permit the protrusions 549 and 551 to be lowered beneath the engagement member 513, at which point the protrusions 549 and 551 move again inwardly beneath the engagement member 513 to lock the female connector 501 in place with respect to the male connector 503. To release the female connector 501 from the male connector 503, one or both of the wings 541 and 545 can be deflected inwardly (e.g., by manually pinching the wings 541 and 545 together toward the connector 529), thereby causing the barbs 543 and 547 to be deflected radially outwardly until the protrusions 549 and 551 are disengaged from the engagement member 513 of the male connector 503. The female connector 501 can then be lifted and separated from the male connector 503.

As noted above, the filter 505 is configured to be received within the receptacle 527 of the female connector 501. In some embodiments, the filter 505 can be an anti-bacterial filter made of foam or other suitable material. The filter 505 can include an upper portion 553 configured to abut against the third opening 532 on the interior of the receptacle 527, and a lower portion 555 configured to be inserted at least partially into the first opening 519 in the male connector 503. In some embodiments, the upper portion 553 be a disc-like member having a diameter substantially corresponding to that of the receptacle 527. The upper portion 553 of the filter 505 can be sized and configured to cover the third opening 532 on the interior surface of the receptacle 527, such that fluid and air flowing through the third opening 532 passes through the filter 505. The lower portion 555 of the filter 505 can have a smaller outer diameter than the upper portion 553, corresponding substantially to the diameter of the lumen 517 of the male connector 503. The O-ring 507 can be positioned to surround the lower portion 555 of the filter 505. When the O-ring 507 is in this position and the filter 505 is compressed between the female connector 501 and male connector 503, the O-ring can ensure a substantially air-tight seal between the filter 505 and the upper portion 509 of the male connector 503. The O-ring 507 may alternatively be held by the male connector 503 in one of the grooves in portion 509 over which the female connector will slide to create a substantially air-tight seal.

In some embodiments, the filter 505 can have a pore size of approximately 0.22 micron, approximately 0.45 micron, approximately 0.8 micron, or approximately 1.2 micron. Furthermore, in some embodiments an additional hydrophobic layer or coating made of polypropylene (e.g., pore size of 0.2 or 0.45 micron) or PTFE (e.g., with a pore size of 0.2 or 0.45 micron) can be added to ensure that no fluids enter the suction device 101 through the connection assembly 500. In some embodiments, the filter 505 can be a two-part or multi-part construction, with a thinner filter (e.g., approximately 0.1 mm) membrane supported mechanically by the use of a rigid felt filter and/or other structural support.

When the female connector 501 is engaged with the male connector 503, a fluidic connection is established across the connection assembly 500. With negative pressure applied (e.g., from the valve assembly 400 to the second opening 523 at the bottom of the connector 515) air can flow from the fourth opening 533, down through the lumen 531 of the female connector 501, through the filter 505, through the lumen 517 of the male connector 503, and through an intervening conduit (not shown) to the valve assembly 400. As all air from the patient and cannister passes through the filter 505, contaminants can be removed, and the device can be maintained in a clean and sterile manner.

The female connector 501 can be easily removed for cleaning and to replace the filter 505 and/or the O-ring 507 as needed. In some embodiments, the female connector 501 and/or the male connector 503 can be made from durable materials to enable reuse after sterilization. For example, in some embodiments the female connector 501 and/or the male connector 503 can be made of plastic, metal, ceramics or composites or other materials useful for mechanical flexures (can deform elastically in the range needed). The connection assembly 500 disclosed herein provides for a reusable filter connection that can be used with a variety of cannister options. Since the connection assembly 500 can connect to a standard tube (via connector 529), the connection assembly 500 (and therefore the suction device 101) can be connected to any rigid port of a generic suction container. The filter disposed within the female connector 501 provides a safety barrier to protect the suction device 101 from contaminants associated with a user-supplied container such as bacterial, viral or fungal pathogens transmitted through air or liquid, or residue on the canister from other use or incomplete cleaning and sterilization.

Selected Embodiments of NPWT Methods

The present technology includes a method comprising selectively actuating a vacuum pump with a square wave in response to analog electronic signals from a sensor to maintain vacuum pressure to be within a therapeutic range for NPWT. The method additionally comprises holding vacuum pressure in the therapeutic range by use of a passive valve assembly such as 400 and limiting the maximum vacuum pressure supplied by the device by use of the same passive valve assembly 400. The method additionally comprises turning indicators on and off within a user interface 207.

The method can be used to operate a device that is similar to the suction device 101 described above. For example, in some embodiments the suction device can include a vacuum connection assembly 500 configured to be fluidically coupled to the canister 111, a pump 317 configured to supply negative pressure to the vacuum connection assembly 500, and a passive valve assembly 400 in fluid communication with the pump 317 and the vacuum connection assembly 500. The passive valve assembly 400 can be configured to maintain the pump 317 in fluid communication with the vacuum connection assembly 500 within a predefined pressure range, and to passively inhibit fluid communication between the pump and the vacuum connection outside of the predefined pressure range.

FIG. 6 illustrates how in some embodiments, the pressure control circuitry 700 may produce a square wave 605, for example, of DC voltage, that turns the pump 317 on and off according to changing vacuum pressure levels 604 in the system. When the device is powered on, the pump is turned on to increase the vacuum pressure inside the device if the device pneumatic system is at ambient pressure. The pump activation during phase 606 causes the vacuum pressure in the system indicated as line 604 to increase from ambient. When the vacuum pressure level reaches the upper threshold 601, which is slightly greater than the specific therapeutic vacuum level prescribed for therapy 602, the pump will turn off 607. The pump will rest until the vacuum pressure level 604 gradually falls (due to leaks in the device or wound dressing) to the point of the lower threshold 603, at which point the pump will turn back on 608. This method is presented in graphs 600 and 605 wherein the x axes 611 and 612 represent time and share the same scale. The y axis 613 represents vacuum pressure and the y axis 610 represents voltage supplied to a pump. Through this simple control method with hysteresis, the system pressure is maintained within a range that averages to the nominal pressure for therapy if the range is centered on the nominal pressure for therapy 602. A benefit of this method is that the pump is turned on and off less often, which reduces the wearing of a brush motor, and disturbs the patient fewer times per hour or day. The larger the range above 601 and below 603 the nominal pressure 602, the less often the pump is turned on during therapy, though the pump will run longer each time it is turned on. The differences between the upper and lower thresholds and the nominal pressure may be between 2.5% and 10%.

In some embodiments, the electronic system described is coupled to the passive valve assembly, in which case the valve can serve both as a check valve and over pressure relief valve. In this case, the vacuum pressure required to open the check valve side should be well below the lower threshold for therapy 603 and the vacuum pressure required to open the pressure relief valve side should be above the upper threshold for therapy 601 and may be well above that threshold, such as 614. The check valve function serves to slow the rate of decay of vacuum pressure in the system, allowing the pump to rest longer as in 607. The passive valve assembly serves an additional safety function when used with the pressure control circuitry 700, sensor 309 and pump 317. A benefit of the pressure control circuitry described is that only one sensor is required for pressure control in the system, which lowers device cost and weight. However, the single sensor 309 could experience a component level failure that could cause the pump to run without control, raising system vacuum pressures to a level that could cause damage to the patient's coupled wound. If the vacuum pressure level required to open the ambient vent of the valve is set below the threshold at which wound damage can occur (for example, 150-200 mmHg), the device will be failsafe to electrical failures in the sensor or other electronic components of the circuitry 700 or pump 317.

In some embodiments, the pressure control circuitry 700 described is coupled to the user interface 207 described in FIG. 2C. The circuitry can be configured such that an LED 214 marked "LOW", or otherwise marked to indicate that vacuum pressure is lower than specified for therapy (e.g. with symbols, minus sign, markings, shapes, letters, and/or icons), is illuminated when the vacuum level is rising and the pump is on as in phase 606, until the rising threshold is met. Additionally, the circuitry can cause an LED 215 marked "OK", or otherwise marked to indicate that vacuum pressure in the device is appropriate for therapy (e.g. with symbols, markings, shapes, letters, and/or icons), to be illuminated when the vacuum level is falling, until the falling threshold 603 is met. Further, the circuitry can be configured such that only one of these two LEDs is illuminated at one time and the maximum rate of state change between them can be between 0.5 and 2 Hz. Additionally, the pressure control circuitry 700 can be configured such that the LED 216 marked HIGH is illuminated if the vacuum pressure in the system exceeds the upper threshold limit 601 or a limit higher than that threshold, such as 614, for example in case of a pump malfunction. The benefit of such an indication method is that an unskilled user can quickly determine the state of the system without requiring prior knowledge of NPWT. Additionally, this method does not allow for user configuration, so therapy is ensured to be provided in the range prescribed for the patient's wound. Finally, this user interface method does not require screens or LCD displays, which would increase complexity, weight, and cost of a device.

In some embodiments, activating the suction device can require only simple on/off activation to start the pressure sensing and square wave generation, without any need for tuning the supplied pressure or selecting from among a variety of input options. This simple on/off activation improves ease-of-use and lowers the barriers to treatment for patients in resource-constrained environments.

Examples

As an example of the present technology used in medical practice, NPWT devices were fabricated that utilize the above-described pump 317 with PCB 301, pressure control circuitry 700 and pressure control scheme outlined in FIG. 6. The device was configured to provide −125 mmHg+/− 10% via microdiaphragm pump with flow rate 0.7 liters/min with the pressure control circuitry 700 above described. Fourteen patients with various open wound types indicated for NPWT were treated with these devices. Patients treated with the devices benefitted from reduction in wound volume from median 47.25 cm$^3$ to median 9.75 cm$^3$ (p=0.01). Granulation tissue surface area increased from median 7.63 cm$^2$ to median 28.73 cm$^2$ (p=0.003). Granulation tissue formation is a known benefit of NPWT. Open wound surface area decreased from median 48.33 cm$^2$ to median 33.6 cm$^2$ (p=0.01). Wound surface area reduction is another benefit of NPWT. As an additional example of the embodiment in practice, when the female connector 501 and male connector 503 were used in a NPWT device prototype as the vacuum connection assembly 500 with a conduit 119 to a canister 111, usability study data collected suggest that the design was usable and allowed for unskilled users to make pneumatic connections as part of NPWT application and monitoring. After a short product briefing, 14 of 14 representative lay person users were able to attach and remove the female connector from the male connector as part of changing a waste canister without assistance. The users were also 100% successful in inserting and connecting a new waste canister with the female connector 501 coupled via conduit such as 119.

CONCLUSION

Although many of the embodiments are described above with respect to systems, devices, and methods for negative pressure wound therapy, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-8.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A suction device for negative pressure wound therapy, the suction device comprising:
   a vacuum connection configured to deliver negative pressure to a treatment site;
   a pump configured to supply negative pressure to the vacuum connection; and
   a passive valve assembly in fluid communication with the pump and the vacuum connection, the passive valve assembly comprising:
   an interior configured to receive negative pressure from the pump;
   an ambient vent outlet;
   a vacuum outlet;

a first moveable occluder configured to close and open the ambient vent outlet with respect to the interior in response to pressure conditions within the interior; and a second moveable occluder configured to close and open the vacuum outlet, wherein the passive valve assembly is configured to maintain the pump in fluid communication with the vacuum connection within a predefined pressure range, and to passively inhibit fluid communication between the pump and the vacuum connection outside of the predefined pressure range.

2. The device of claim 1, wherein the passive valve assembly further comprises a sensor outlet; and wherein the second moveable occluder is additionally configured to close and open the sensor outlet with respect to the interior in response to pressure conditions within the interior.

3. The device of claim 1, wherein, in the absence of applied negative pressure from the pump, both the first moveable occluder and the second moveable occluder are closed.

4. The device of claim 1, wherein, in the presence of negative pressure within the predefined pressure range, the second moveable occluder opens the vacuum outlet with respect to the interior, and the first moveable occluder closes the ambient vent outlet with respect to the interior.

5. The device of claim 1, wherein, the presence of negative pressure having a greater magnitude than the predefined pressure range, the first moveable occluder opens the vent outlet with respect to the interior.

6. The device of claim 1, further comprising a pressure sensor electrically coupled to the pump and in fluid communication with the valve assembly, wherein the pressure sensor is in analog electronic communication with a circuit network of other analog electronic logic components and integrated circuits, wherein none of the integrated circuits are microcontrollers or microprocessors.

7. The device of claim 6, wherein the circuit network comprises a logic module that utilizes one or more comparators with hysteresis with a set point and reset point within the predefined pressure range.

8. The device of claim 1, wherein the vacuum connection comprises:
a male connector secured to the suction device;
a female connector removably coupleable to the male connector; and
a filter disposed between the female connector and the male connector.

9. The device of claim 8, wherein the male connector is in fluid communication with the passive valve assembly, and wherein the female connector comprises a connector configured to engage with a conduit.

10. The device of claim 8, wherein the female connector comprises an engagement mechanism including a first wing coupled to a first barb and a second wing coupled to a second barb, and wherein the male connector comprises an engagement member, the first and second barbs configured to mate with the engagement member to secure the female connector and the male connector together.

11. The device of claim 10, wherein inwardly deflecting the first and second wings releases the first and second barbs from the engagement member.

12. The device of claim 8, further comprising a waste canister removably coupled to a housing of the device without moving pieces, wherein the housing is configured to accommodate non-specific waste canisters in different rotational positions.

13. The device of claim 1, wherein the predefined pressure range includes −125 mmHg.

14. The device of claim 1, wherein the device does not include a microprocessor or microcontroller.

15. The device of claim 1, wherein the predefined pressure range is not adjustable by a user.

16. A method of applying negative pressure wound therapy, the method comprising:
(a) disposing a wound dressing over a wound site on a patient;
(b) fluidically coupling the wound dressing to a canister;
(c) fluidically coupling the canister to a suction device, thereby establishing a fluidic pathway;
(d) fluidically connecting a pressure sensor to a passive valve assembly of the suction device, wherein the passive valve assembly comprises:
an interior configured to receive negative pressure from the suction device;
an ambient vent outlet;
a vacuum outlet;
a sensor outlet;
a first moveable occluder configured to close and open the ambient vent outlet with respect to the interior in response to pressure conditions within the interior; and
a second moveable occluder configured to close and open the vacuum outlet with respect to the interior in response to pressure conditions within the interior,
(e) supplying power to the suction device;
(f) determining pressure in the fluidic pathway using the pressure sensor;
(g) comparing the pressure to an upper threshold and a lower threshold;
(h) powering on a pump of the suction device until the pressure meets the upper threshold;
(i) after (h), powering off the pump until the pressure falls to the lower threshold;
(j) repeating steps (f)-(g) to maintain the pressure in the fluidic pathway between the upper threshold and the lower threshold;
(k) limiting the maximum pressure in the fluidic pathway with the passive valve assembly;
(l) preventing backflow in the fluidic pathway; and
(m) terminating therapy by removing power to the suction device and relieving pressure in the fluidic pathway.

17. The method of claim 16, wherein the upper threshold is between 5-15% greater than a therapeutic vacuum level for therapy and the lower threshold is between 5-15% lower than the therapeutic vacuum level for therapy.

18. The method of claim 16, further comprising:
providing a first indication signifying that the pressure is lower than specified for therapy while the pressure is rising until the pressure reaches the upper threshold; and
providing a second indication signifying that the pressure is within a therapeutic range while the pressure is falling until the pressure reaches the lower threshold.

19. The method of claim 16, wherein a center of a range bounded by the upper and lower thresholds is 125 mmHg.

* * * * *